(12) United States Patent
Yang et al.

(10) Patent No.: US 7,354,709 B2
(45) Date of Patent: Apr. 8, 2008

(54) COLLAPSIN RESPONSE MEDIATOR PROTEIN-1

(75) Inventors: Pan-Chyr Yang, Taipei (TW); Jin-Yuan Shih, Taipei (TW); Jeremy J. W. Chen, Fengyuan (TW); Konan Peck, Taipei (TW); Cheng-Wen Wu, Taipei (TW); Tse-Ming Hong, Taipei (TW); Shuenn-Chen Yang, Taipei (TW)

(73) Assignees: National Taiwan University, Taipei (TW); Academia Sinica, Taipei (TW); National Health Research Institutes, Taipei (TW)

( * ) Notice: Subject to any disclaimer, the term of this patent is extended or adjusted under 35 U.S.C. 154(b) by 561 days.

(21) Appl. No.: 10/180,198

(22) Filed: Jun. 25, 2002

(65) Prior Publication Data

US 2003/0077624 A1    Apr. 24, 2003

Related U.S. Application Data

(60) Provisional application No. 60/301,075, filed on Jun. 26, 2001.

(51) Int. Cl.
*C12Q 1/68* (2006.01)
(52) U.S. Cl. .............................. 435/6; 530/350; 436/64; 536/23.5
(58) Field of Classification Search .................... 435/6; 536/23.5; 530/350; 436/64
See application file for complete search history.

(56) References Cited

U.S. PATENT DOCUMENTS

| | | | |
|---|---|---|---|
| 6,504,010 B1* | 1/2003 | Wang et al. | ................. 530/350 |
| 2002/0172952 A1* | 11/2002 | Henderson et al. | ............ 435/6 |
| 2004/0009154 A1* | 1/2004 | Khan et al. | ............... 424/93.21 |

FOREIGN PATENT DOCUMENTS

| WO | WO 98/37192 | 8/1998 |
|---|---|---|
| WO | WO 02/04514 | 1/2002 |

OTHER PUBLICATIONS

De Plaen et al. (Immunogenetics. 1994; 40: 360-369).*
Skolnick et al. (Trends in Biotechnology. 2000; 18: 34-39).*
Ward (Developmental Oncology. 1985; 21: 91-106).*
Critchfield (Disease Markers. 1999; 15: 108-111).*
Sidransky (Science. 1997; 278: 1054-1058).*
Tockman et al (Cancer Research. 1992; 52: 2711s-2718s).*
Rae et al. (International Journal of Cancer. 2000; 88: 726-732).*
Chen et al. (Mol. Cell. Proteomics. 2002 Apr; 1 (4): 304-313).*
Liu et al. (Cancer J. 2001 Sep-Oct; 7 (5): 395-403).*
GenBank:AAH48980 PRKAA1 protein *Homo sapiens*, Starusberg et al: "Direct Submission", XP002245204; retrieved from NCBI, Apr. 22, 2003.

GenBank:Q14194, *Homo sapiens*, "Dihydropirimidinase related protein-1 (DRP-1) (Collapsin response mediator protein-1) (CRMP-1)" retrieved from SWISSPROT Database accession No. Q14194 XP002257597; Sep. 2003.
Mammalian Gene Collection Program Team: "Generation and Initial Analysis of More than 15,000 Full-length Human and Mouse cDNA Sequences", *PNAS*, vol. 99, No. 26, pp. 16899-16903; 2002.
Shih, Jin-Yuan et al: "Collapsin response mediator protein-1 and the Invasion of Metastasis of Cancer Cells." *Journal of the National Cancer Institute*, vol. 93, No. 18, pp. 1392-1400, XP009018841; 2001.
Shih, Jin-Yuan et al: "Collapsin Response Mediator Protein-1: A Novel Invasion-Suppressor Gene.", *Clinical and Experimental Metastasis*, vol. 20, pp. 69-76, XP009018804; 2003.
Steeg, Patricia S.: "Collapsin Response Mediator Protein-1: A Lung Cancer Invasion Suppressor Gene with Nerve" *Journal of the National Cancer Institute*, vol. 93, No. 18, pp. 1364-1365, 2001; XP009018842.
Albelda et al., "Integrin distribution in malignant melanoma: association of the $\beta_3$ subunit with tumor progression", *Cancer Res.* 50:6757-6764 (1990).
Albrecht-Buehler, "Filopodia of spreading 3T3 cells", *J Cell Biol* 69:275-286 (1976).
Alizadeh et al., "Distinct types of diffuse large B-cell lymphoma identified by gene expression profiling", *Nature* 403:503-11 (2000).
Ballestrem et al., "Actin-dependent lamellipodia formation and microtubule-dependent tail retraction control-directed cell migration", *Mol Biol Cell* 11:2999-3012 (2000).
Bieche et al., "Real-time reverse transcription-PCR assay for future management of ERBB2-based clinical applications", *Clin Chem* 45:1148-1156 (1999).
Birch et al., "Isolation and characterization of human melanoma cell variants expressing high and low levels of CD44", *Cancer Res.* 51:6660-6667 (1991).
Brambilla et al., "Semaphorin SEMA3F localization in malignant human lung and cell lines: A suggested role in cell adhesion and cell migration", *Am J Pathol* 156:939-950 (2000).
Byk et al., "Identification and molecular characterization of unc-33-like phosphoprotein (Ulip), a putative mammalian homology of the axonal guidance-associated unc-33 gene product", *J Neurosci* 16:688-701 (1996).
Byk et al., "The Ulip family phosphoproteins: common and specific properties", *Eur J Biochem* 254:14-24 (1998).
Chen et al., "Global analysis of gene expression in invastion by a lung cancer model", *Cancer Res.* 61:5223-5230 (2001).
Chen et al., "Profiling expression patterns and isolating differentially expressed genes by cDNA microarray system with colorimetry detection", *Genomics* 51:313-324 (1998).
Chien et al., "Navigational errors made by growth cones without filopodia in the embryonic *Xenopus* brain", *Neuron* 11:237-251 (1993).

(Continued)

*Primary Examiner*—Stephen L. Rawlings
(74) *Attorney, Agent, or Firm*—Fei-Fei Chao; Andrews Kurth LLP

(57) ABSTRACT

This invention is based on the discovery of an association of Collapsin Response Mediator Protein-1 (CRMP-1) with tumor metastasis. The level of CRMP-1 protein or mRNA can be used as an indicator of cellular invasiveness and of a test compound's ability to alter cellular invasiveness. The level of CRMP-1 protein can also be altered, e.g., to reduce invasiveness.

4 Claims, No Drawings

OTHER PUBLICATIONS

Chu et al., "Selection of invasive and metastatic subpopulations from a human lung adenocarcinoma cell line", *Am J Respir Cell Mol Biol* 17:353-360 (1997).

Clark et al., "Genomic analysis of metastasis reveals an essential role for RhoC", *Nature* 406:532-535 (2000).

Cooper, "The role of actin polymerization in cell motility", *Ann Rev Physiol* 53:585-605 (1991).

Denizot and Lang, "Rapid colorimetric assay for cell growth and survival: modifications to the tetrazolium dye procedure giving improved sensitivity and reliability", *J Immunol Methods* 89:271-277 (1986).

Denko et al., "Epigenetic regulation of gene expression in cervical cancer cells by the tumor microenvironment", *Clin. Cancer Res.* 6:480-487 (2000).

Dong et al., "KAII, a metastasis suppressor gene for prostate cancer on human chromosome 11p11.2", *Science* 268:884-886 (1995).

Fildler and Kripke, "Metastasis results from preexisting variant cells within a malignant tumor", *Science* 197:893-895 (1977).

Friedrichs et al., "High expression level of α6 integrin in human breast carcinoma is correlated with reduced survival", *Cancer Res.* 55:901-906 (1995).

Fukada et al., "Molecular characterization of CRMP5, a novel member of the collapsin response mediator protein family", *J Biol Chem.* 275:3795737965 (2000).

Gaetano et al., "Identification and characterization of a retinoic acid-regulated human homologue of the umc-33-like phosphoprotein (hUlip) from neuroblastoma cells", *J Biol Chem* 272:12195-12201 (1997).

Gehlsen et al., "Inhibition of in vitro cell invasion by *Arg-Gly-Asp*-containing synthetic peptides", *J. Cell. Biol.* 106:925-930 (1988).

Goldberg et al., "Human 72-kilodalton type IV collagenase forms a complex with a tissue inhibitor of metalloproteinases designated TIMP-2", *Proc. Natl. Acad. Sci. USA* 86:8207-8211 (1989).

Golub et al., "Molecular classification of cancer: class discovery and class prediction by gene expression monitoring", *Science* 286:531-537 (1999).

Goshima et al., "Collapsin-induced growth cone collapse mediated by an intracellular protein related to unc-33", *Nature* 376:509-514 (1995).

Gu et al., "Neurofibrillary tangle-associated collapsin response mediator protein-2 (CRMP-2) is highly phosphorylated on Thr-509 Ser-518, and Ser-522", *Biochemistry* 39:4267-4275 (2000).

Gu and Ihara, "Evidence that collapsin response mediator protein-2 is involved in the dynamics of microtubules", *J Biol Chem* 275:17917-17920 (2000).

Hamajima et al., "A novel gene family defined by human dihydropyridinase and three related proteins with differential tissue distribution", *Gene* 180:157-163 (1996).

Harn et al., "Soluble CD44 isoforms in serum as potential markers of metastatic gastric carcinoma", *J. Clin. Gastroenterol.* 22:107-110 (1996).

Hong et al., "Profiling the downstream genes of tumor suppressor PTEN in lung cancer cells by complementary DNA microarray", *Am J Respir Cell Mol Biol* 23:355-363 (2000).

Hsu and White, "BRCA1 is associated with the centrosome during mitosis", *Proc Natl Acad Sci USA* 95:1298312988 (1998).

Hudson et al., "Urokinase and the urokinase receptor: association with in vitro invasiveness of human bladder cancer cell lines", *J. Natl. Cancer Inst.* 89:709-717 (1997).

Inagaki et al., "Differential expression of dihydropyrimidinase-related protein genes in developing and adult enteric nervous system", *Histochem Cell Biol* 113:37-41 (2000).

Ito et al., "Repulsive axon guidance molecule Sema3A inhibits branching morphogenesis of fetal mouse lung", *Mech Dev* 97:35-45 (2000).

Ito et al., "Expression of the Axl receptor tyrosine kinase in human thyroid carcinoma", *Thyroid* 9:563-567 (1999).

Iyer et al., "The transcriptional program in the response of human fibroblasts to serum", *Science* 283:83-87 (1999).

Jacob et al., "A receptor tyrosine kinase, UFO/Axl, and other genes isolated by a modified differential display PCR are overexpressed in metastatic prostatic carcinoma cell line DU145", *Cancer Detect. Prev.* 23:325-332 (1999).

Kanamori et al., "Correlation between expression of the *matrix mellaproteinase-I gene* in ovarian cancers and an insertion/deletion polymorphism in its promoter region", *Cancer Res.* 59:4225-4227 (1999).

Khan et al., "Expression profiling in cancer using cDNA microarrays", *Electrophoresis* 20:223-229 (1999).

Khanna et al., "Metastasis-associated differences in gene expression in a murine model of osteosarcoma", *Cancer Res.* 61:3750-3759 (2001).

Kodera et al., "Expression of nm23 H-1 RNA levels in human gastric cancer tissues. A negative correlation with nodal metastasis", *Cancer* 73:259-265 (1994).

Kohn, "Development and prevention of metastasis", *Anticancer Res* 13:2553-2560 (1993).

Kriajevska et al., "Metastasis-associated Mts1 (S100A4) protein modulated protein kinase C phosphorylation of the heavy chain of nonmuscle myosin", *J. Biol. Chem.* 273:9852-9856 (1998).

Lee et al., "KiSS-1. a novel human malignant melanoma metastasis-suppressor gene", *J Natl Cancer Inst* 88:17311737 (1996).

Liao et al., "Low concentrations of nocodazole interfere with fibroblast locomotion without significantly affecting microtubule level: implications for the role of dynamic microtubules in cell locomotion", *J Cell Sci* 108:3473-3483 (1995).

Liotta et al., "Cancer metastasis and angiogenesis: an imbalance of positive and negative regulation", *Cell* 64:327-336 (1991).

Marken et al., "Cloning and expression of the tumor-associated antigen L6", *Proc. Natl. Acad. Sci. USA* 89:3503-3507 (1992).

Martin-Satué and Blanco, "Identification of semaphorin E gene expression in metastatic human lung adenocarcinoma cells by mRNA differential display", *J Surg Oncol* 72:18-23 (1999).

Matsuo et al., "Structure and promoter analysis of the human *unc-33*-like phosphoprotein gene: E-box required for maximal expression in neuroblastoma and myoblasts", *J Biol Chem* 275:16560-16568 (2000).

Miao et al., "Neuropiln-1 mediates collapsin-1/semaphorin III inhibition of endothelial cell motility: functional competition of collapsin-1 and vascular endothelial growth factor-165", *J Cell Biol* 146:233-241 (1999).

Minturn et al., "TOAD-64, a gene expressed early in neuronal differentiation in the rat, is related to *unc-33*, a *C. elegans* gene involved in axon outgrowth", *J Neurosci* 15:6757-6766 (1995).

Mitchison and Cramer, "Actin-based cell motility and cell locomotion", *Cell* 84:371-379 (1996).

Miyake et al., "Elevation of urokinase-type plasminogen activator and its receptor densities as new predictors of disease progression and prognosis in men with prostate cancer", *Int. J. Oncol.* 14:535-541 (1999).

Morini et al., "The α3β1 integrin is associated with mammary carcinoma cell metastasis, invasion, and gelatinase B (MMP-9) activity", *Int. J. Cancer* 87:336-342 (2000).

Morris et al., "p53 localized to the centrosomes and spindles of mitotic cells in the embryonic chick epiblast, human cell lines, and a human primary culture: an immunofluorescence study", *Exp Cell Res* 256:122-130 (2000).

Okada et al., "A novel in vitro assay system for transendothelial tumor cell invasion: significance of E-selectin and α3 integrin in the transendothelial invasion by HT1080 fibrosarcoma cells", *Clin. Exp. Metastas,* 12:305-314 (1994).

Perou et al., "Molecular portraits of human breat tumours", *Nature* 406:747-752 (2000).

Powell et al., "Expression of the metalloproteinase matrilysin in DU-145 cells increases their invasive potential in server combined immunodeficient mice", *Cancer Res.* 53:417-422 (1993).

Quach et al., "Collapsin response mediator protein-3/unc-33-like protein-4 gene: organization, chromosomal mapping and expression in the developing mouse brain", *Gene* 242:175-182 (2000).

Quinn et al., "A Family of Proteins Implicated in Axon Guidance and Outgrowth", *J. Neurobiol* 41:158-164 (1999).

Raper, "Semaphorins and their receptors in vertebrates and invertebrates", *Curr Opin Neurobiol* 10:88-94 (2000).

Ridley, "Molecular switches in metastasis", *Nature* 406:466-467 (2000).

Robbins et al., "Two interdependent basic domains in nucleoplasmin nuclear targeting sequence: identification of a class of bipartite nuclear targeting sequence", *Cell* 64:615-623 (1991).

Roche et al., "Distinct 3p21.3 deletions in lung cancer and identification of a new human semaphoring", *Oncogene* 12:1289-1297 (1996).

Ross et al., "Systematic variation in gene expression patterns in human cancer cell lines", *Nat Genet* 24:227-235 (2000).

Schuler, "Pieces of the puzzle: expressed sequence tags and the catalog of human genes", *J. Mol. Med.* 75:694-698 (1997).

Sekido et al., "Human semaphorins A(V) and IV reside in the 3p21.3 small cell lung cancer deletion region and demonstrate distinct expression patterns", *Proc. Natl. Acad. Sci. USA* 93:4120-4125 (1996).

Shan et al., "Molecular cloning of cellular genes encoding retinoblastoma-associated proteins: identification of a gene with properties of the transcription factor E2F", *Mol Cell Biol* 12:5620-5631 (1992).

Shi et al., "Cooperation between transcription factor AP-1 and NF-κB in the induction of interleukin-8 in human pancreatic adenocarcinoma cells by hypoxia", *J. Interf. Cytok. Res.* 19:1363-1371 (1999).

Sreenath et al., "Expression of matrix metalloproteinase genes in transformed rate cell lines of high and low metastatic potential", *Cancer Res.* 52:4942-4947 (1992).

Steeg et al., "Evidence for a novel gene associated with low tumor metastatic potential", *J Natl Cancer Inst* 80:200-204 (1988).

Suwa et al., "Overexpression of the rhoC gene correlates with progression of ductal adenocarcinoma of the pancreas", *Brit. J. Cancer* 77:147-152 (1998).

Symons and Mitchison, "Control of actin polymerization in live and permeabilized fibroblasts", *J Cell Biol* 114:503-513 (1991).

Takahashi et al., "Plexin-neuropilin-1 complexes form functional sema-phorin-3A receptors", *Cell* 99:59-69 (1999).

Tamayo et al., "Interpreting patterns of gene expression with self-organizing maps: methods and application to hematopoietic differentiation", *Proc. Natl. Acad. Sci. USA* 96:2907-2912 (1999).

Tokunaga et al., "Thrombospondin 2 expression is correlated with inhibition of angiogenesis and metastasis of colon cancer", *Brit. J. Cancer* 79:354-359 (1999).

Torres and Polymeropoulos, "Genomic organization and localization of human CRMP-1 gene", *DNA Res* 5:393-395 (1998).

Vleminckx et al., "Genetic manipulation of E-cadherin expression by epithelial tumor cells reveals an invasion suppressor role", *Cell* 66:107-119 (1991).

Wang and Strittmatter, "A family of rat CRMP genes is differentially expressed in the nervous system", *J NeuroSci* 16:6197-6207 (1996).

Wang and Strittmatter, "Brain CRMP forms heterotetramers similar to liver dihydropyrimidinase", *J Neurochem* 69:2261-2269 (1997).

Weterman et al., "Expression of calcyclin in human melanoma cell lines correlates with metastatic behavior in nude mice", *Cancer Res.* 52:1291-1296 (1992).

Wewer et al., "Altered levels of laminin receptor mRNA in various human carcinoma cells that have different abilities to bind laminin", *Proc. Natl. Acad. Sci. USA* 83:7137-7141 (1986).

Woodhouse et al., "General mechanisms of metastasis", *Cancer* Supplement 80:1529-1537 (1997).

Xiang et al., "Isolation of the human semaphorin III/F gene (SEMA3F) at chromosome 3p21, a region deleted in lung cancer", *Genomics* 32:39-48 (1996).

Yoneda et al., "Development of high-density DNA microarray membrane for profiling smoke- and hydrogen peroxide-induced genes in a human bronchial epithelial cell line", *Am J Respir Crit Care Med.* 164:S85-S89 (2001).

Yoshida et al., "Metastasis-suppressor genes: a review and perspective", *J Natl Cancer Inst* 92:1717-1730 (2000).

Yu et al., "CRMP-5 neuronal autoantibody: marker of lung cancer and thymoma-related autoimmunity", *Ann Neurol* 49:146-154 (2001).

Yuan et al., "Interleukin-8 messenger ribonucleic acid expression correlates with tumor progression, tumor angiogenesis, patient survival, and timing of relapse in non-small-cell lung cancer", *Am J Respir Crit Care Med* 162:1957-1963 (2000).

* cited by examiner

COLLAPSIN RESPONSE MEDIATOR PROTEIN-1

CROSS-REFERENCE TO RELATED APPLICATIONS

This application claims priority to U.S. application Ser. No. 60/301,075, filed Jun. 26, 2001, the contents of which is hereby incorporated by reference in its entirety for all purposes.

BACKGROUND

Collapsin Response Mediator Proteins (CRMPs) are a family of phosphoproteins that may mediate semaphorin/collapsin-induced growth cone collapse and are involved in axonal guidance and neuronal differentiation. See, for example, Goshima et al. (1995) *Nature* 376: 509-14; Fukada et al. (2000) *J Biol Chem.* 275: 37957-65; Minturn et al. (1995) *J Neurosci* 15: 6757-66; Wang & Stittmatter (1996) *J NeruoSci* 16: 6197-207; Byk et al. (1996) *J Neurosci* 16: 688-701; and Gaetano et al. (1997) *J Biol Chem* 272: 12195-201.

Five members (CRMP-1, CRMP-2, CRMP-3, CRMP-4, and CRMP-5) of the CRMP family related to 60-66 kDa proteins have been independently cloned by several different laboratories pursuing different goals. One characterized function of proteins of the CRMP family is the repulsive guidance of nerve axons. The functional role of the CRMPs in this process has been studied (Quinn et al. (1999) *J Neurobiol* 41: 158-64). The CRMPs have about 50%-70% amino acid sequence homology among the five family members (Hamajima et al. (1996) *Gene* 180: 157-63), and they have been proposed to form heterotetramers through mutual associations (Wang & Stittmatter (1997) *J Neurochem* 69: 2261-9). However, each of the CRMPs displays a distinct expression pattern during development in the nervous system and in response to nerve growth factor induction of neuronal differentiation (Byk et al. (1998) *Eur J Biochem* 254: 14-24).

CRMP-2 was found associated with neruofibrillary tangles in Alzheimer's patients (Gu et al. (2000) *Biochemistry* 39: 4267-75). CRMP-3 and CRMP-5 were recognized by autoantibodies in patients of small cell lung cancers with paraneoplastic neurological syndrome (Yu et al. (2001) *Ann Neurol* 49: 146-54; and Honnorat et al. (1999) *Eur J Neurosci* 11: 4226-32).

SUMMARY

This invention is based on the discovery that Collapsin Response Mediator Protein-1 (CRMP-1) is associated with at least some kinds of tumor metastasis. An exemplary nucleotide sequence of the CRMP-1 coding region is recited as follows:

```
ATGTCGTACC AGGGCAAGAA GAGCATCCCG CACATCACGA GTGACCGACT CCTCATCAAA    60   (SEQ ID NO:1)

GGTGGACGGA TCATCAACGA TGACCAATCC CTTTATGCTG ACGTCTACCT GGAGGATGGA   120

CTTATCAAAC AAATAGGAGA GAACTTAATC GTTCCTGGTG GAGTGAAGAC CATTGAAGCC   180

AACGGGCGGA TGGTTATTCC CGGAGGTATT GATGTCAACA CGTACCTGCA GAAGCCCTCC   240

CAGGGGATGA CTGCGGCTGA TGACTTCTTC CAAGGGACCA GGGCGGCACT GGTGGGCGGG   300

ACCACGATGA TCATTGACCA TGTTGTTCCT GAACCTGGGT CCAGCCTACT GACCTCTTTC   360

GAGAAGTGGC ACGAAGCAGC TGACACCAAA TCCTGCTGTG ATTACTCCCT CCACGTGGAC   420

ATCACAAGCT GGTACGATGG CGTTCGGGAG GAGCTGGAGG TGCTGGTGCA GGACAAAGGC   480

GTCAATTCCT TCCAAGTCTA CATGGCCTAT AAGGATGTCT ACCAAATGTC CGACAGCCAG   540

CTCTATGAAG CCTTTACCTT CCTTAAGGGC CTGGAGCTG TGATCTTGGT CCATGCAGAA    600

AATGGAGATT TGATAGCTCA GGAACAAAAG CGGATCCTGG AGATGGGCAT CACGGGTCCC   660

GAGGGCCATG CCCTGAGCAG ACCTGAAGAG CTGGAGGCCG AGGCGGTGTT CCGGGCCATC   720

ACCATTGCGG GCCGGATCAA CTGCCCTGTG TACATCACCA AGGTCATGAG CAAGAGTGCA   780

GCCGACATCA TCGCTCTGGC CAGGAAGAAA GGGCCCCTAG TTTTTGGAGA GCCCATTGCC   840

GCCAGCCTGG GGACCGATGG CACCCATTAC TGGAGCAAGA ACTGGGCCAA GGCTGCGGCG   900

TTCGTGACTT CCCCTCCCCT GAGCCCGGAC CCTACCACGC CCGACTACTT GACCTCCCTA   960

CTGGCCTGTG GGGACTTGCA GGTCACAGGC AGCGGCCACT GTCCCTACAG CACTGCCCAG  1020

AAGGCGGTGG GCAAGGACAA CTTTACCCTG ATCCCCGAGG GTGTCAACGG GATAGAGGAG  1080

CGGATGACCG TCGTCTGGGA CAAGGCGGTG GCTACTGGCA AAATGGATGA GAACCAGTTT  1140

GTCGCTGTCA CCAGCACCAA TGCAGCCAAG ATCTTTAACC TGTACCCAAG GAAAGGGCGG  1200

ATTGCCGTGG GCTCGGATGC CGACGTGGTC ATCTGGGACC CCGACAAGTT GAAGACCATA  1260

ACAGCCAAAA GTCACAAGTC GGCGGTGGAG TACAACATCT TCGAGGGTAT GGAGTGCCAC  1320
```

```
                                          -continued
GGCTCCCCAC  TAGTGGTCAT  CAGCCAGGGC  AAGATCGTCT  TTGAAGACGG  AAACATCAAC  1380

GTCAACAAGG  GCATGGGCCG  CTTCATTCCG  CGGAAGGCGT  TCCCGGAGCA  CCTGTACCAG  1440

CGCGTCAAAA  TCAGGAATAA  GGTTTTTGGA  TTGCAAGGGG  TTTCCAGGGG  CATGTATGAC  1500

GGTCCTGTGT  ACGAGGTACC  AGCTACACCC  AAATATGCAA  CTCCCGCTCC  TTCAGCCAAA  1560

TCTTCGCCTT  CTAAACACCA  GCCCCCACCC  ATCAGAAACC  TCCACCAGTC  CAACTTCAGC  1620

TTATCAGGTG  CCCAGATAGA  TGACAACAAT  CCCAGGCGCA  CCGGCCACCG  CATCGTGGCG  1680

CCCCCTGGTG  GCCGCTCCAA  CATCACCAGC  CTCGGTTGA                          1719
```

The amino acid sequence of CRMP-1 is recited as follows:

(SEQ ID NO:2)
MSYQGKKSIPHITSDRLLIKGGRIINDDQSLYADVYLEDGLIKQIGENLI

VPGGVKTIEANGRMVIPGGIDVNTYLQKPSQGMTAADDFFQGTRAALVGG

TTMIIDHVVPEPGSSLLTSFEKWHEAADTKSCCDYSLHVDITSWYDGVRE

ELEVLVQDKGVNSFQVYMAYKDVYQMSDSQLYEAFTFLKGLGAVILVHAE

NGDLIAQEQKRILEMGITGPEGHALSRPEELEAEAVFRAITIAGRINCPV

YITKVMSKSAADIIALARKKGPLVFGEPIAASLGTDGTHYWSKNWAKAAA

FVTSPPLSPDPTTPDYLTSLLACGDLQVTGSGHCPYSTAQKAVGKDNFTL

IPEGVNGIEERMTVVWDKAVATGKMDENQFVAVTSTNAAKIFNLYPRKGR

IAVGSDADVVIWDPDKLKTITAKSHKSAVEYNIFEGMECHGSPLVVISQG

KIVFEDGNINVNKGMGRFIPRKAFPEHLYQRVKIRNKVFGLQGVSRGMYD

GPVYEVPATPKYATPAPSAKSSPSKHQPPPIRNLHQSNFSLSGAQIDDNN

PRRTGHRIVAPPGGRSNITSLG

CRMP-1 is also described in SWISS-PROT entry Q14194, GenBank™ locus D78012, and GenBank™ locus BAA11190. It is also referred to as dihydropyrimidinase related protein-1 (DRP-1).

In one aspect, this invention features a method for supplying a therapeutic polypeptide to a subject. The method includes identifying a subject in need of treatment to prevent, attenuate, or arrest a tumor metastasis; providing a cell which includes an exogenous nucleic acid that encodes a polypeptide having the amino acid sequence of SEQ ID NO:2 or a functional fragment thereof; allowing the human cell to express a polypeptide; and administering the polypeptide to the subject. The cell can be a human cell, such as a human fibroblast. The subject can be a human or an experimental mammal.

The term "functional fragment" used herein refers to a nucleic acid or a polypeptide having at least one activity of a polypeptide encoded by SEQ ID NO:2, e.g., inhibiting tumor metastasis. Whether a fragment is functional can be determined by expressing the fragment in $CL_{1-5}$ lung carcinoma cells and evaluating the ability of the transformed cells to invade the basement membrane in an in vitro reconstituted basement membrane invasion assay. A functional fragment will inhibit the invasive phenotype of the $CL_{1-5}$ lung carcinoma cells.

A CRMP-1 nucleic acid has a sequence selected from the group consisting of (1) a nucleic acid containing a sequence which is at least 80% identical to the nucleotide sequence of SEQ ID NO:1; (2) a nucleic acid containing a fragment of at least 150 nucleotides of the nucleotide sequence of SEQ ID NO:1; (3) a nucleic acid which encodes a polypeptide containing the amino acid sequence of SEQ ID NO:2; and (4) a nucleic acid which encodes a fragment of a polypeptide containing the amino acid sequence of SEQ ID NO:2, wherein the fragment includes at least 50 amino acids of SEQ ID NO:2. A CRMP-1 polypeptide has a sequence selected from the group consisting of (1) a polypeptide containing a sequence which is at least 80% identical to the amino acid sequence of SEQ ID NO:2; (2) a fragment containing the amino acid sequence of SEQ ID NO:2, wherein the fragment includes at least 50 amino acids of SEQ ID NO:2; (3) a polypeptide which is encoded by a nucleic acid containing the nucleotide sequence of SEQ ID NO:1; and (4) a polypeptide encoded by a nucleic acid which is at least 80% identical to the nucleotide sequence of SEQ ID NO:1. In some embodiments, the therapeutic polypeptide can be an antibody or an antigen-binding fragment thereof, which reacts with, or specifically binds a CRMP-1 polypeptide.

In another aspect, this invention features a first method for treating tumor metastasis in a subject. The method includes identifying a subject in need of treating tumor metastasis; providing a cell which includes an exogenous nucleic acid that encodes a polypeptide having the amino acid sequence of SEQ ID NO:2 or a functional fragment thereof; and allowing the cell to express a polypeptide in vivo in the subject, thereby treating tumor metastasis in the subject.

In a related aspect, this invention also features a second method for treating tumor metastasis in a subject. The method includes identifying a subject in need of treating tumor metastasis; and introducing a cell into the subject, the cell including an exogenous nucleic acid that encodes a polypeptide having the amino acid sequence of SEQ ID NO:2 or a functional fragment thereof, and competent to express the polypeptide in an amount sufficient to ameliorate a symptom of tumor metastasis, thereby treating tumor metastasis in the subject.

In still another aspect, the invention features a method for diagnosing tumor invasive potential or metastasis in a subject. The method includes providing a sample from a subject; determining the level of expression of CRMP-1 in the sample; comparing the sample expression to a reference expression value; and categorizing the subject as having tumor invasive potential or metastasis when the sample expression is lower than the reference expression. Each of the sample expression or the reference expression is an assessment of the abundance of (1) an mRNA transcribed from a CRMP-1 nucleic acid; or (2) a CRMP-1 polypeptide. The CRMP-1 polypeptide can be detected, e.g., using an antibody, e.g., the Y21 antibody. This method also can be used to (1) monitor a subject during tumor treatment; or (2) monitor a treatment for tumor metastasis in a subject.

The reference expression value can be arbitrary or associated with a reference sample or a reference state. The reference sample can be one or more of: (1) a sample from a normal subject; (2) a sample from an in vitro cell, e.g., a cancer cell line, e.g., a lung adenocarcinoma line, e.g., a cell line described herein; (3) a sample from a subject having a metastatic disorder and undergoing treatment; and (4) a sample from a subject being evaluated, e.g., an earlier sample or a normal sample of the same subject. In monitoring a treatment, the method further includes comparing the sample CRMP-1 polypeptide level or CRMP-1 nucleic acid expression level to a level obtained from the subject prior to treatment or prior to onset of the disorder. In some embodiments, the subject CRMP-1 polypeptide level or CRMP-1 nucleic acid expression level is determined at intervals (e.g., regular intervals) during treatment.

The expression level of a CRMP-1 gene product or mRNA can be determined along with the expression level of at least 10, 50, 100, or 1000 other genes or gene products. For example, U.S. application Ser. No. 60/300,991, filed Jun. 26, 2001, describes other genes whose expression levels are useful to monitor.

In another aspect, this invention features a method for identifying a test compound useful in the prevention or treatment of tumor metastasis. This method includes steps of contacting a cell with a test compound; and determining whether the test compound modulates the expression of a CRMP-1 nucleic acid or a CRMP-1 polypeptide in the cell. The test compound can be an agonist of a CRMP-1 polypeptide. The term "agonist", as used herein, refers to a molecule which, when bound to CRMP-1 polypeptide, increases or prolongs the duration of the effect of CRMP-1.

The test compound can be a macromolecule or a small molecule, such as a molecule having a molecular weight less than about 10,000 grams per mole, an organic or inorganic compound having a molecular weight less than about 5,000 grams per mole, an organic or inorganic compound having a molecular weight less than about 1,000 grams per mole, an organic or inorganic compound having a molecular weight less than about 500 grams per mole. Examples of macromolecules include a polypeptide, a protein complex, or a nucleic acid (e.g., DNA, RNA, or peptide nucleic acid). Examples of small molecules include a peptide, a peptidomimetic (e.g., s peptoid), an amino acid, an amino acid analog, an oligonucleotide, an oligonucleotide analog, a nucleotide, a nucleotide analog, an organic or inorganic compound (e.g., heteroorganic or organometallic compound).

This invention also features a pharmaceutical composition for treating tumor metastasis. The composition includes an effective amount of an agent and a pharmaceutically acceptable carrier. The agent can be a CRMP-1 polypeptide, a CRMP-1 nucleic acid, or a test compound that modulates the level of expression of CRMP-1, wherein the expression of CRMP-1 is an assessment of the abundance of (1) an mRNA transcribed from a CRMP-1 nucleic acid; or (2) a CRMP-1 polypeptide. The pharmaceutical composition can include a delivery agent, e.g., a liposome or viral vector. The composition or delivery agent can be attached to a tumor targeting moiety, e.g., an antibody against a tumor specific antigen. The invention also features an antibody that binds to a polypeptide comprising the amino acid sequence of SEQ ID NO:2. For example, the antibody can be an antibody described herein, or a functional fragment thereof, e.g., an antigen binding fragment.

In another aspect, the invention features a genetic construct that includes a marker gene encodes a marker protein. The marker gene is operably linked to a CRMP-1 regulatory sequence, e.g., the CRMP-1 promoter. In one embodiment, the marker gene is an in-frame fusion to at least a segment of the CRMP-1 coding sequence. The construct can be used in a method of assessing CRMP-1 gene expression. The method can include contacting a cell that includes the genetic construct with a test compound and assessing the abundance and/or presence of the marker protein. The invention also features a host cell that includes the genetic construct, e.g., a mammalian cell, e.g., a lung carcinoma cell.

Also within the scope of this invention is the use of the just-described agent for the manufacture of a medicament for treating tumor metastasis.

The details of one or more embodiments of the invention are set forth in the description below. Other features, objects, and advantages of the invention will be apparent from the description and from the claims.

DETAILED DESCRIPTION

CRMP-1: a Metastasis-Associated Gene

A model system containing clonally related cell lines has been developed from a human lung adenocarcinoma cell line. The cell lines, such as $CL_{1-0}$ and its sublines (e.g., $CL_{1-1}$ and $CL_{1-5}$) have different invasion capabilities from each other both in vitro and in vivo. To identify genetic determinants correlated with tumor metastasis, a cDNA microarray containing 9,600 different nucleic acid probes was used to characterize the mRNA expression levels of genes, and, thus, identify metastasis-associated genes. Among the identified metastasis-associated genes, the expression levels of the CRMP-1 gene and gene product were inversely correlated with the invasive capability of lung cancer cell lines. CRMP-1 was expressed to a lesser extent in the more invasive cell lines. Northern hybridization and Western blotting with a specific monoclonal antibody against CRMP-1 have been used to confirm this inverse correlation. The association of CRMP-1 expression and tumor metastasis was further investigated in several lung cancer tissues using real-time quantitative reverse transcription PCR. Over-expression of CRMP-1 by transfection in a highly invasive cell line decreased filapodia formation and suppressed the in vitro invasive ability. CRMP-1 polypeptides are dynamically distributed within cells and can be localized with mitotic spindles and centrosomes. Low expression of CRMP-1 mRNA in lung cancer tissue is significantly associated with advanced tumor (stage III or IV), lymph node metastasis, early post-operative relapse, and shorter survival.

CRMP-1 Polypeptides, Nucleic Acids, and CRMP-1-Specific Antibodies

CRMP-1 polypeptides can be used for a variety of processes. For example, the CRMP-1 polypeptides can be used to screen for substrates of CRMP-1 polypeptide substrates, to screen compounds which modulate CRMP-1 activity, as well as to treat disorders characterized by reduced CRMP-1 activity, e.g., at least some tumor metastases, e.g. a lung carcinoma.

A CRMP-1 polypeptide can be isolated from cells or tissue sources using standard protein purification techniques, e.g., in combination with recombinant DNA expression techniques. A CRMP-1 polypeptide can be expressed in a heterologous system, e.g., a cultured cell or a transgenic animal. Expression in the heterologous system may result in substantially the same post-translational modifications as in a native cell. The sequence of a CRMP-1 polypeptide can differ from SEQ ID:2, for example, by at least one but by less than 15, 10 or 5 amino acid residues. Alternatively, it differs from the corresponding sequence in SEQ ID NO:2 by at least one residue but less than 20%, 15%, 10% or 5% of the residues in it. The differences can be at a non-essential residue or a conservative substitution.

Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; a group of amino acids having acidic side chains is aspartic acid, glutamic acid, and histidine; and a group of amino acids having sulfur-containing side chains is cysteine and methionine. Depending on circumstances, amino acids within the same group may be interchangeable. Some additional conservative amino acids substitution groups are: valine-leucine-isoleucine; phenylalanine-tyrosine;, lysine-arginine; alanine-valine; and asparagine-glutamine.

CRMP-1 nucleic acids can be used, for example, to express CRMP-1 polypeptides (e.g., in a host cell or in a cell of an organism), to detect CRMP-1 mRNAs (e.g., in a biological sample) or genetic alterations in CRMP-1 genes, and to modulate CRMP-1 polypeptide activity. A CRMP-1 nucleic acid can include a fragment that can be used as a probe or primer to detect or amplify a CRMP-1 nucleic acid or a CRMP-1 fragment encoding a portion of a CRMP-1 polypeptide, e.g., an immunogenic or biologically active portion of a CRMP-1 polypeptide. The fragment can include a sequence corresponding to a domain, region, or a functional site. CRMP-1 probes and primers are also provided. Typically a probe/primer is an isolated or purified oligonucleotide. The oligonucleotide typically includes a region of nucleotide sequence that hybridizes under a stringency condition described herein to at least about 7, 12 or 15, or about 20, 25, 30, 35, 40, 45, 50, 55, 60, 65, or 75 consecutive nucleotides of a sense or antisense sequence of SEQ ID NO:1. A CRMP-1 nucleic acid encompasses a nucleic acid molecule that differs from the nucleotide sequence shown in SEQ ID NO:1. Such a difference can be due to degeneracy of the genetic code and result in a nucleic acid which encodes the same CRMP-1 polypeptide. A CRMP-1 nucleic acid has a nucleotide sequence encoding a protein having an amino acid sequence which differs, by at least 1, but less than 5, 10, 20, or 50 amino acid residues that shown in SEQ ID NO:2.

CRMP-1-specific antibodies, or fragments thereof (e.g., antigen-binding fragments thereof) can be used to detect and isolate CRMP-1 polypeptides, regulate the bioavailability of CRMP-1 polypeptides, and modulate CRMP-1 activity. The term "antibody" as used herein refers to an immunoglobulin molecule or immunologically active portion thereof, i.e., an antigen-binding fragment. The term "immunoglobulin" refers to a protein consisting of one or more polypeptides substantially encoded by immunoglobulin genes. The recognized human immunoglobulin genes include the kappa, lambda, alpha (IgA1 and IgA2), gamma (IgG1, IgG2, IgG3, IgG4), delta, epsilon and mu constant region genes, as well as the myriad immunoglobulin variable region genes.

A CRMP-1-specific antibody can be generated using methods that are well known in the art. Such an antibody may include, but is not limited to, polyclonal, monoclonal, chimeric, a single chain, a Fab fragment, and a fragment produced by a Fab expression library. A monoclonal antibody to CRMP-1 may be prepared using any technique which provides for the production of an antibody molecule by a continuous cell line in culture. Examples of the techniques are the hybridoma technique, the human B-cell hybridoma technique, and the EBV-hybridoma technique (Kohler et al. (1975) Nature 256: 495-497; Kozbor et al. (1985) J. Immunol. Methods 81: 31-42; Cote et al. (1983) Proc. Natl. Acad. Sci. USA 80: 2026-2030; or Cole et al. (1984) Mol. Cell Biol. 62: 109-120). In addition, techniques developed for the production of "chimeric antibodies", the splicing of mouse antibody genes to human antibody genes to obtain a molecule with appropriate antigen specificity and biological activity can be used (Morrison et al. (1984) Proc. Natl. Acad. Sci. USA 81: 6851-6855; Neuberger et al. (1984) Nature 312: 604-608; or Takeda et al. (1985) Nature 314: 452-454). Alternatively, techniques described for the production of single chain antibodies may be adapted, using methods known in the art, to produce CRMP-1-specific single chain antibodies. A CRMP-1-specific antibody can also be produced by inducing in vivo production in the lymphocyte population or by screening immunoglobulin libraries or panels of highly specific binding reagents as disclosed in the literature (Orlandi et al. (1989) Proc. Natl. Acad. Sci. USA 86: 3833-3837; or Winter et al. (1991) Nature 349: 293-299).

For the production of a CRMP-1-specific antibody, various hosts including goats, rabbits, rats, mice, humans, and others, may be immunized by injection with a CRMP-1 polypeptide. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. A CRMP-1-specific antibody can be a fully human antibody, e.g., an antibody made in a mouse which has been genetically engineered to produce an antibody from a human immunoglobulin sequence, or a non-human antibody, e.g., a rodent (mouse or rat), goat, primate (e.g., monkey), camel antibody. Methods of producing rodent antibodies are known in the art. See, for example, Wood et al. International Application WO 91/00906; Kucherlapati et al. PCT publication WO 91/10741; Lonberg et al. International Application WO 92/03918; or Kay et al. International Application 92/03917. A CRMP-1-specific antibody can be one in which a variable region, or a portion thereof is generated in a non-human organism, e.g., a rat or mouse. An antibody generated in a non-human organism, e.g., a rat or mouse, and then modified, e.g., in the variable framework or constant region, to decrease antigenicity in a human is also within the invention.

A full-length CRMP-1 polypeptide or, an antigenic peptide fragment of a CRMP-1 polypeptide can be used as an immunogen or can be used to identify CRMP-1-specific antibodies made with other immunogens, e.g., cells, membrane preparations, and the like. The antigenic peptide of a CRMP-1 polypeptide should include at least 8 amino acid residues of the amino acid sequence shown in SEQ ID NO:2 and encompasses an epitope of a CRMP-1 polypeptide. The antigenic peptide can include at least 10, 15, 20, or 30 amino acid residues of the CRMP-1 polypeptide.

Therapeutics

A CRMP-1 polypeptide can be used as a part of a gene therapy protocol to deliver nucleic acids encoding either an agonistic or antagonistic form of a CRMP-1 polypeptide. The invention features expression vectors for in vivo transfection and expression of a CRMP-1 polypeptide in particular cell types so as to reconstitute the function of, or alternatively, antagonize the function of a CRMP-1 polypeptide in a cell in which that polypeptide is misexpressed. Expression constructs of CRMP-1 polypeptides, may be administered in any biologically effective carrier, e.g. any formulation or composition capable of effectively delivering the CRMP-1 gene to cells in vivo. The expression constructs can include a nucleic acid sequence encoding a CRMP-1 polypeptide operatively linked to a heterologous promoter, e.g., an inducible promoter. The gene therapy protocol can include administering an inducer of the inducible promoter to the subject.

Approaches include insertion of the subject gene in viral vectors including recombinant retroviruses, adenovirus, adeno-associated virus, and herpes simplex virus-1, or recombinant bacterial or eukaryotic plasmids. Viral vectors transfect cells directly; plasmid DNA can be delivered with the help of, for example, cationic liposomes (lipofectin) or derivatized (e.g. antibody conjugated), polylysine conjugates, gramacidin S, artificial viral envelopes or other such intracellular carriers, as well as direct injection of the gene construct or $CaPO_4$ precipitation carried out in vivo.

An approach for in vivo introduction of a CRMP-1 nucleic acid into a cell can be by use of a viral vector containing nucleic acid, e.g. a cDNA, encoding a CRMP-1 polypeptide. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells which have taken up viral vector nucleic acid.

Retrovirus vectors and adeno-associated virus vectors can be used as a recombinant gene delivery system for the transfer of exogenous genes in vivo, particularly into humans. These vectors provide efficient delivery of genes into cells, and the transferred nucleic acids are stably integrated into the chromosomal DNA of the host. The development of specialized cell lines (termed "packaging cells") which produce only replication-defective retroviruses has increased the utility of retroviruses for gene therapy, and defective retroviruses are characterized for use in gene transfer for gene therapy purposes (for a review see Miller, A. D. (1990) *Blood* 76:271). A replication defective retrovirus can be packaged into virions which can be used to infect a target cell through the use of a helper virus by standard techniques. Protocols for producing recombinant retroviruses and for infecting cells in vitro or in vivo with such viruses can be found in *Current Protocols in Molecular Biology*, Ausubel, F. M. et al. (eds.) Greene Publishing Associates, (1989), Sections 9.10-9.14 and other standard laboratory manuals. Examples of suitable retroviruses include pLJ, pZIP, pWE and pEM which are known to those skilled in the art. Examples of suitable packaging virus lines for preparing both ecotropic and amphotropic retroviral systems include yCrip, yCre, y2 and yAm. Retroviruses have been used to introduce a variety of genes into many different cell types, including epithelial cells, in vitro and/or in vivo (see for example Eglitis, et al. (1985) *Science* 230: 1395-1398; Danos and Mulligan (1988) *Proc. Natl. Acad. Sci. USA* 85: 6460-6464; Wilson et al. (1988) *Proc. Natl. Acad. Sci. USA* 85: 3014-3018; Armentano et al. (1990) *Proc. Natl. Acad. Sci. USA* 87: 6141-6145; Huber et al. (1991) *Proc. Natl. Acad. Sci. USA* 88: 8039-8043; Ferry et al. (1991) *Proc. Natl. Acad. Sci. USA* 88: 8377-8381; Chowdhury et al. (1991) *Science* 254: 1802-1805; van Beusechem et al. (1992) *Proc. Natl. Acad. Sci. USA* 89: 7640-7644; Kay et al. (1992) *Human Gene Therapy* 3: 641-647; Dai et al. (1992) *Proc. Natl. Acad. Sci. USA* 89: 10892-10895; Hwu et al. (1993) *J. Immunol.* 150:4104-4115; U.S. Pat. No. 4,868,116; U.S. Pat. No. 4,980,286; PCT Application WO 89/07136; PCT Application WO 89/02468; PCT Application WO 89/05345; and PCT Application WO 92/07573).

Another useful viral gene delivery system includes an adenovirus-derived vector. The genome of an adenovirus can be manipulated such that it encodes and expresses a gene product of interest but is inactivated in terms of its ability to replicate in a normal lytic viral life cycle. See, for example, Berkner et al. (1988) *Bio Techniques* 6: 616; Rosenfeld et al. (1991) *Science* 252: 431-434; and Rosenfeld et al. (1992) *Cell* 68: 143-155. Suitable adenoviral vectors derived from the adenovirus strain Ad type 5 d1324 or other strains of adenovirus (e.g., Ad2, Ad3, Ad7 etc.) are known to those skilled in the art. Recombinant adenoviruses can be advantageous in certain circumstances in that they are not capable of infecting nondividing cells and can be used to infect a wide variety of cell types, including epithelial cells (Rosenfeld et al. (1992) cited supra). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situ where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham (1986) *J. Virol.* 57: 267).

Yet another viral vector system useful for delivery of a CRMP-1 gene is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al. (1992) *Curr. Topics in Micro. and Immunol.* 158: 97-129). It is also one of the few viruses that may integrate its DNA into non-dividing cells, and exhibits a high frequency of stable integration (see for example Flotte et al. (1992) *Am. J. Respir. Cell. Mol. Biol.* 7: 349-356; Samulski et al. (1989) *J. Virol.* 63: 3822-3828; and McLaughlin et al. (1989) *J. Virol.* 62: 1963-1973). Vectors containing as little as 300 base pairs of AAV can be packaged and can integrate. Space for exogenous DNA is limited to about 4.5 kb. An AAV vector such as that described in Tratschin et al. (1985) *Mol. Cell. Biol.* 5: 3251-3260 can be used to introduce DNA into cells. A variety of nucleic acids have been introduced into different cell types using AAV vectors (see for example Hermonat et al. (1984) *Proc. Natl. Acad. Sci. USA* 81: 6466-6470; Tratschin et al. (1985) *Mol. Cell. Biol.* 4: 2072-2081; Wondisford et al. (1988) *Mol. Endocrinol.* 2: 32-39; Tratschin et al. (1984) *J. Virol* 51: 611-619; and Flotte et al. (1993) *J. Biol. Chem.* 268: 3781-3790).

In addition to viral transfer methods, such as those illustrated above, non-viral methods can also be employed to cause expression of a CRMP-1 polypeptide in the tissue of an animal. Most nonviral methods of gene transfer rely on normal mechanisms used by mammalian cells for the uptake and intracellular transport of macromolecules. In some embodiments, non-viral gene delivery systems of the present invention rely on endocytic pathways for the uptake of a CRMP-1 nucleic acid by the targeted cell. Exemplary gene delivery systems of this type include liposomal derived systems, poly-lysine conjugates, and artificial viral envelopes. Other embodiments include plasmid injection systems such as are described in Meuli et al. (2001) *J. Invest Dermatol.* 116(1): 131-135; Cohen et al. (2000) *Gene Ther* 7(22): 1896-905; or Tam et al. (2000) *Gene Ther* 7(21): 1867-74.

In a representative embodiment, a nucleic acid encoding a CRMP-1 polypeptide can be entrapped in liposomes bearing positive charges on their surface (e.g., lipofectins) and (optionally) which are tagged with antibodies against cell surface antigens of the target tissue (Mizuno et al. (1992) *No Shinkei Geka* 20: 547-551; PCT publication WO91/06309; Japanese patent application 1047381; and European patent publication EP-A-43075).

In clinical settings, the gene delivery systems for the therapeutic CRMP-1 nucleic acid can be introduced into a patient by any of a number of methods, each of which is familiar in the art. For instance, a pharmaceutical preparation of the gene delivery system can be introduced systemically, e.g. by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g. Chen et al. (1994) *PNAS* 91: 3054-3057).

The pharmaceutical preparation of the gene therapy construct can consist essentially of the gene delivery system in an acceptable diluent, or can comprise a slow release matrix in which the gene delivery vehicle is imbedded. Alternatively, where the complete gene delivery system can be produced in tact from recombinant cells, e.g. retroviral vectors, the pharmaceutical preparation can comprise one or more cells which produce the gene delivery system.

Diagnosis

This invention also provides a method for diagnosing tumor invasive potential or metastasis in a subject. This method can also be used to (1) monitor a subject during a treatment; or (2) evaluate a subject suspected of having a tumor disorder or known to have a tumor disorder.

The method includes obtaining a sample (e.g., a biopsy, blood, or other tissue sample) from a subject; determining the level of expression of CRMP-1 in the sample; comparing the sample expression to a reference expression value; and categorizing the subject as having tumor invasive potential or metastasis when the sample expression is lower than the reference expression. Each of the sample expression or the reference expression is an assessment of the abundance of (1) an mRNA transcribed from a CRMP-1 nucleic acid; or (2) a CRMP-1 polypeptide. The sample includes tissues, cells and biological fluids isolated from a subject, as well as tissues, cells and fluids present within a subject. An example of the sample is serum.

The level of expression of the CRMP-1 gene can be measured by the level of mRNA corresponding to the CRMP-1 gene in a cell. The measurement can be determined both by in situ and by in vitro assays, such as hybridization or amplification assays, which include, but are not limited to, Northern analyses, polymerase chain reaction analyses and probe arrays. One diagnostic method for the detection of mRNA levels involves contacting the mRNA with a nucleic acid probe that can hybridize to the mRNA encoded by the gene being detected. The nucleic acid probe can be, for example, a full-length CRMP-1 nucleic acid, such as the nucleic acid of SEQ ID NO:1, or a portion thereof, such as an oligonucleotide of at least 7, 15, 30, 50, 100, 250 or 500 nucleotides in length and sufficient to specifically hybridize under stringent conditions to CRMP-1 mRNA or genomic DNA. The probe can be disposed on an address of an array. Other suitable probes for use in the diagnostic assays are described herein. In one format (such as a Northern blot), mRNA (or cDNA) is immobilized on a surface and contacted with the probes, for example by running the isolated mRNA on an agarose gel and transferring the mRNA from the gel to a membrane, such as nitrocellulose. In an alternative format, the probes are immobilized on a surface and the mRNA (or cDNA, e.g., labeled cDNA) is contacted with the probes, for example, in a two-dimensional gene chip array described below. A skilled artisan can adapt known mRNA detection methods for use in detecting the level of mRNA encoded by the CRMP-1 genes.

The level of mRNA in a sample can also be evaluated with nucleic acid amplification, e.g., by rtPCR (Mullis (1987) U.S. Pat. No. 4,683,202), ligase chain reaction (Barany (1991) *Proc. Natl. Acad. Sci. USA* 88:189-193), self sustained sequence replication (Guatelli et al, (1990) *Proc. Natl. Acad. Sci. USA* 87:1874-1878), transcriptional amplification system (Kwoh et al., (1989), *Proc. Natl. Acad. Sci. USA* 86:1173-1177), Q-Beta Replicase (Lizardi et al., (1988) *Bio/Technology* 6:1197), rolling circle replication (Lizardi et aL, U.S. Pat. No. 5,854,033) or any other nucleic acid amplification method, followed by the detection of the amplified molecules using techniques known in the art. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

A variety of methods can be used to determine the level of a CRMP-1 polypeptide. In general, these methods include contacting an agent that selectively binds to the CRMP-1 polypeptide, such as an antibody with a sample, to evaluate the level of the polypeptide in the sample. The antibody can bear a detectable label. The term "labeled," with regard to the probe or antibody, is intended to encompass direct labeling of the probe or antibody by coupling (i.e., physically linking) a detectable substance to the probe or antibody, as well as indirect labeling of the probe or antibody by reactivity with a detectable substance.

The detection methods can be used to detect a CRMP-1 polypeptide in a sample in vitro as well as in vivo. In vitro techniques for detection of a CRMP-1 polypeptide include enzyme linked immunosorbent assays (ELISAs), immunoprecipitations, immunofluorescence, enzyme immunoassay (EIA), radioimmunoassay (RIA), and Western blot analysis. In vivo techniques for detection of a CRMP-1 polypeptide include introducing into a subject a labeled a CRMP-1- specific antibody. For example, the antibody can be labeled with a radioactive marker whose presence and location in a subject can be detected by standard imaging techniques. In another embodiment, the sample is labeled, e.g., biotinylated and then contacted to the antibody. The sample can be detected, e.g., with avidin coupled to a fluorescent label.

For in situ methods, a cell or tissue sample can be prepared/processed and immobilized on a support, typically a glass slide, and then contacted with a probe that can hybridize to mRNA that encodes the CRMP-1 gene being analyzed. Diagnostic and prognostic assays can further include contacting a control sample with a compound or agent capable of detecting CRMP-1 mRNA, or genomic DNA, and comparing the presence of CRMP-1 mRNA or genomic DNA in the control sample with the presence of CRMP-1 mRNA or genomic DNA in the test sample. Serial analysis of gene expression, as described in U.S. Pat. No. 5,695,937, can also be used to detect CRMP-1 transcript levels.

Screening a Test Compound

The invention provides a method for identifying a test compound, i.e., a candidate or an agent that modulates the level of expression a CRMP-1 nucleic acid or a CRMP-1 polypeptide.

The test compounds can be obtained using any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive; see, e.g., Zuckermann et al. (1994) *J. Med. Chem.* 37: 2678-85); spatially addressable parallel solid phase or solution phase libraries; synthetic library methods requiring deconvolution; the "one-bead one-compound" library method; and synthetic library methods using affinity chromatography selection. The biological library and peptoid library approaches are limited to peptide libraries, while the other four approaches are applicable to peptide, non-peptide oligomer or small molecule libraries of compounds (Lam (1997) *Anticancer Drug Des.* 12: 145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233.

Libraries of compounds may be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner, U.S. Pat. No. 5,223,409), spores (Ladner U.S. Pat. No. 5,223,409), plasmids (Cull et al. (1992) *Proc Natl Acad Sci USA* 89:1865-1869) or on phage (Scott and Smith (1990) *Science* 249:386-390; Devlin (1990) *Science* 249:404-406; Cwirla et al. (1990) *Proc. Natl. Acad. Sci.* 87:6378-6382; Felici (1991) *J. Mol. Biol.* 222:301-310; Ladner supra.). Exemplary combinatorial chemical libraries include, but are not limited to, peptide libraries (see, e.g., U.S. Pat. No. 5,010,175, Furka, *Int. J. Pept. Prot. Res.* 37:487-493 (1991) and Houghton et al., *Nature* 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al, *Nature Biotechnology,* 14(3): 309-314 (1996) and PCT/US96/10287), carbohydrate libraries (see, e.g., Liang et al., *Science,* 274:1520-1522 (1996) and U.S. Pat. No. 5,593,853), small organic molecule libraries (see, e.g., benzodiazepines, Baum C&EN, Jan 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

A test compound modulating the CRMP-1 nucleic acid expression can be identified. For example, a cell or cell free mixture is contacted with a test compound and the expression of CRMP-1 mRNA or polypeptide evaluated relative to the level of expression of CRMP-1 mRNA or polypeptide in the absence of the test compound. When expression of CRMP-1 mRNA or polypeptide is greater in the presence of the test compound than in its absence, the test compound is identified as a stimulator of CRMP-1 mRNA or polypeptide expression. Alternatively, when expression of CRMP-1 mRNA or polypeptide is less (e.g., statistically significantly less) in the presence of the test compound than in its absence, the candidate compound is identified as an inhibitor of CRMP-1 mRNA or polypeptide expression. The level of CRMP-1 mRNA or polypeptide expression can be determined by methods described above in "Diagnoses".

The ability of a test compound to modulate a CRMP-1 polypeptide binding to a substrate, e.g., a CRMP-1 substrate, can be evaluated. This can be accomplished, for example, by coupling the substrate with a radioisotope or enzymatic label such that binding of the substrate to the CRMP-1 polypeptide can be determined by detecting the labeled substrate in a complex. Alternatively, a CRMP-1 polypeptide can be coupled with a radioisotope or enzymatic label to monitor the ability of a test compound to modulate the CRMP-1 polypeptide binding to a CRMP-1 polypeptide substrate in a complex. For example, a substrate can be labeled with $^{125}$I, $^{35}$S, $^{14}$C, or $^{3}$H, either directly or indirectly, and the radioisotope detected by direct counting of radioemmission or by scintillation counting. Alternatively, a test compound can be enzymatically labeled with, for example, horseradish peroxidase, alkaline phosphatase, or luciferase, and the enzymatic label detected by determination of conversion of an appropriate substrate to a product.

The ability of a test compound to interact with a CRMP-1 polypeptide with or without the labeling of any of the interactants can be evaluated. For example, an interaction between a test compound and a CRMP-1 polypeptide can be detected using fluorescence energy transfer (FET) (see, for example, Lakowicz et al., U.S. Pat. No. 5,631,169; Stavrianopoulos, et al., U.S. Pat. No. 4,868,103). A fluorophore label on the first, "donor" molecule is selected such that its emitted fluorescent energy will be absorbed by a fluorescent label on a second, "acceptor" molecule, which in turn is able to fluoresce due to the absorbed energy. Labels are chosen that emit different wavelengths of light, such that the "acceptor" molecule label may be differentiated from that of the "donor." Since the efficiency of energy transfer between the labels is related to the distance separating the molecules, the spatial relationship between the molecules can be assessed. An FET binding event can be conveniently measured through standard fluorometric detection means well known in the art (e.g., using a fluorimeter). An interaction between a test compound and a CRMP-1 polypeptide can be accomplished using real-time Biomolecular Interaction Analysis (BIA) (see, e.g., Sjolander, S. and Urbaniczky, C. (1991) Anal. Chem. 63: 2338-2345 and Szabo et al. (1995) Curr. Opin. Struct. Biol. 5: 699-705). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

The method for identifying a test compound pertains to a combination of two or more of the assays described herein, and to novel compounds identified by the above-described screening methods. Accordingly, it is within the scope of this invention to further use a compound identified as described herein (e.g., a CRMP-1 modulating compound, an antisense CRMP-1 nucleic acid molecule, a CRMP-1-specific antibody, or a CRMP-1-binding partner)in an appropriate animal model to determine the efficacy, toxicity, side effects, or mechanism of action, of treatment with such an agent. Furthermore, novel compounds identified by the above-described screening assays can be used for treatments as described herein.

It is also possible to identify a chimeric, artificial zinc finger protein that binds to a CRMP-1 nucleic acid, e.g., a CRMP-1 non-coding region or a CRMP-1 coding region (e.g., a sequence in GenBank™ NT 006051 which includes the CRMP-1 gene, e.g., a sequence in between nucleotides 559971 . . . 635062 or between 540000 . . . 640000). It is possible to generate libraries that include varied zinc finger domains. See, e.g., Rebar et al. (1996) Methods Enzymol 267:129; Greisman and Pabo (1997) Science 275:657; Isalan et al. (2001) Nat. Biotechnol 19:656; and Wu et al. (1995) Proc. Nat. Acad. Sci. USA 92:344.

It is also possible to prepare one or more chimeric zinc finger DNA binding regions, e.g., by selection in vitro (e.g., using phage display) or by design based on a recognition code (see, e.g., WO 00/42219). The zinc finger protein can be fused to a transcriptional activation domain to activate transcription of CRMP-1. The zinc finger protein can itself be encoded by a heterologous nucleic acid that is delivered to a cell. The sequence encoding the zinc finger protein can be operably linked to an inducible promoter, e.g., to enable fine control of the level of the zinc finger protein in the cell.

High Throughput Screening

A high-throughput method can be used to screen large libraries of chemicals. Such libraries of candidate compounds can be generated or purchased e.g., from Chembridge Corp., San Diego, Calif. Libraries can be designed to cover a diverse range of compounds. For example, a library can include 10,000, 50,000, or 100,000 or more unique compounds. Merely by way of illustration, a library can be constructed from heterocycles including pyridines, indoles, quinolines, furans, pyrimidines, triazines, pyrroles, imidazoles, naphthalenes, benzimidazoles, piperidines, pyrazoles, benzoxazoles, pyrrolidines, thiphenes, thiazoles, benzothiazoles, and morpholines. Alternatively, prior experimentation and anecdotal evidence, can suggest a class or category of compounds of enhanced potential. A library can be designed and synthesized to cover such a class of chemicals.

Metastastic cells from the model cell lines (e.g., $CL_{1-0}$ and its sublines, such as $CL_{1-1}$ and $CL_{1-5}$), or cells from tumor metastasis patients, can be used for high throughput drug screening. For example, the cells can be grown in small microtiter plates, e.g., 6-well, 32-well, 64-well, 96-well, 384-well plates. High density microtiter plates can be fashioned from a polymer, e.g., polydimethylsiloxane, (e.g., Sylgard 384 from Dow-Corning) and an acrylic mold. The mold contains wells for the growth of cells into which compounds can be dispensed. For example, a mold can contain 1536 wells with a 2 µL capacity, or 6144 wells with a 250 nL capacity. A plurality of test compounds, or a library as described above, can be screened. The library can be provided in a format that is amenable for robotic manipulation, e.g., in microtiter plates. Compounds can be added to metastastic cells in microtiter plates. Following compound addition, cells are incubated for a specific time. Then, the expression levels are monitored.

The test compounds can also be pooled, and the pools tested. Positive pools are split for subsequent analysis. Regardless of the method, that compounds that alter the expression level of CRMP-1 genes are considered "candidate" compounds or drugs. Candidate compounds are retested on metastastic cells as described above. Candidate compounds that are positive in a retest are considered "lead" compounds.

Once a lead compound has been identified, standard principles of medicinal chemistry can be used to produce derivatives of the compound. Derivatives can be screened for improved pharmacological properties, for example, efficacy, pharmacokinetics, stability, solubility, and clearance. The moieties responsible for a compound's activity in the above described assays can be delineated by examination of structure-activity relationships (SAR) as is commonly practiced in the art. A person of ordinary skill in pharmaceutical chemistry could modify moieties on a lead compound and measure the effects of the modification on the efficacy of the compound to thereby produce derivatives with increased potency. For an example, see Nagarajan et al. (1988) J. Antibiot. 41: 1430-8. A modification can include N-acylation, amination, amidation, oxidation, reduction, alkylation, esterification, and hydroxylation. Furthermore, if the biochemical target of the lead compound is known or determined, the structure of the target and the lead compound can inform the design and optimization of derivatives. Molecular modeling software is commercially available (e.g., Molecular Simulations, Inc.).

Pharmaceutical Compositions

The present invention provides a pharmaceutical composition for treating a subject at risk of (or susceptible to) tumor metastasis or treating a subject having tumor metastasis. As used herein, the term "treatment" is defined as the application or administration of an agent to a patient, or application or administration of an agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease. An agent includes, but is not limited to, a CRMP-1 polypeptide, a CRMP-1 nucleic acid, or a test compound that modulates the expression or effect of a CRMP-1 nucleic acid or a CRMP-1 polypeptide.

A pharmaceutical composition includes the just described agent and a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

An agent can be formulated to be compatible with its intended route of administration. Examples of routes of administration include parenteral, e.g., intravenous, intradermal, subcutaneous, oral (e.g., inhalation), transdermal (topical), transmucosal, and rectal administration. Formulation into dosage forms for these routes of administration can utilize conventional methods. For example, an agent can be formulated in a capsule, a gel seal, or a tablet for oral administration. Capsules may contain any standard pharmaceutically acceptable materials such as gelatin or cellulose. Tablets may be formulated in accordance with conventional procedures by compressing mixtures of an agent with a solid carrier and a lubricant. Examples of solid carriers include starch and sugar bentonite. An agent can also be administered in a form of a hard shell tablet or a capsule containing a binder, e.g., lactose or mannitol, a conventional filler, and a tableting agent.

The pharmaceutical composition may be administered via the parenteral route, including orally, topically, subcutaneously, intraperitoneally, intramuscularly, and intravenously. Examples of parenteral dosage forms include aqueous solutions, isotonic saline or 5% glucose of the active agent, or other well-known pharmaceutically acceptable excipient. Solubilizing agents such as cyclodextrins, or other solubilizing agents well-known to those familiar with the art, can be utilized as pharmaceutical excipients for delivery of the therapeutic agent.

Toxicity and therapeutic efficacy of an agent can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit high therapeutic indices are preferred. While an agent that exhibits toxic side effects may be used, care should be taken to design a delivery system that targets such agent to the site of affected tissue in order to minimize potential damage to uninfected cells and, thereby, reduce side effects.

The data obtained from the cell culture assays and animal studies can be used in formulating a range of dosage for use in humans. The dosage of an agent lies preferably within a range of circulating concentrations that include the $ED_{50}$ with little or no toxicity. The dosage may vary within this range depending upon the dosage form employed and the route of administration utilized. For any agent used in the methods of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of a polypeptide (i.e., an effective dosage) ranges from about 0.001 to 30 mg/kg body weight, about 0.01 to 25 mg/kg body weight, about 0.1 to 20 mg/kg body weight, or about 1 to 10 mg/kg, 2 to 9 mg/kg, 3 to 8 mg/kg, 4 to 7 mg/kg, or 5 to 6 mg/kg body weight. A skilled artisan will appreciate that certain factors may influence the dosage and timing required to effectively treat a subject, including but not limited to the severity of the disease or disorder, previous treatments, the general health and/or age of the subject, and other diseases present.

For antibodies, the preferred dosage is 0.1 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration are often possible. Modifications such as lipidation can be used to stabilize antibodies and to enhance uptake and tissue penetration (e.g., into the brain). A method for lipidation of antibodies is described by Cruikshank et al. ((1997) *J. Acquired Immune Deficiency Syndromes and Human Retrovirology* 14:193).

The present invention encompasses a compound that modulates expression or activity of a CRMP-1 nucleic acid or a CRMP-1 polypeptide. An agent may, for example, be a small molecule. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

The pharmaceutical compositions can be included in a container, pack, or dispenser together with instructions for administration.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications, including patents, cited herein are hereby incorporated by reference in their entirety.

EXAMPLE

Methods

Cells Lines and Culture Conditions. Human lung adenocarcinoma cell lines $CL_{1-0}$, $CL_{1-1}$, $CL_{1-5}$, and $CL_{1-5}$-$F_4$ were grown in RPMI-1640 medium (GIBCO-BRL, Gaithersburg, Md.) with 10% fetal bovine serum (GIBCO-BRL, Gaithersburg, Md.) and 2 mM L-glutamine (GIBCO-BRL, Gaithersburg, Md.) at 37° C., 20% $O_2$, and 5% $CO_2$. $CL_{1-0}$ is the parent cell line; $CL_{1-1}$ and $CL_{1-5}$ are sublines selected from $CL_{1-0}$ by in vitro selection with polycarbonate membrane coating with Matrigel (Collaborative Biomedical, Becton Dickinson, Bedford, Mass.) in a Transwell invasion chamber (Chu et al. (1997) *Am J Respir Cell Mol Biol* 17: 353-60). $CL_{1-5}$ cells were injected into the tail veins of severe combined immunodeficient mice, then a cell line was isolated and cloned from the tumor formed in the lung of mice. After four-repeated in vivo selection, the cell line was designated as $CL_{1-5}$-$F_4$. The adherent cells were detached from the culture dishes using trypsin/EDTA (Sigma, Deisenhofen, Germany). Prior to functional assays, 0.02% EDTA was alternatively used to avoid the destruction of cell surface antigens.

Microarray Analysis. Microarray experiments with 9600 feature arrays on nylon membranes were performed as described by Chen et al. using calorimetric detection method. See Chen et al. (1998) *Genomics* 51: 313-24; and Hong et al. (2000) *Am J Respir Cell Mol Biol* 23: 355-63. Briefly, each cell line grew to 80% confluence and mRNA was isolated 24 hours after cultured cells were changed to fresh medium. The time between removal from the incubator and lysis of the cells was minimized. The total cellular RNA was extracted from cells with a modified guanidinium thiocyanate-phenol-chloroform extraction method using RNAzol B (Biotecx Laboratories, Houston, Tex.). Messenger RNAs were extracted using oligotex-dT resin (Qiagen, Hilden, Germany). Five µg of the mRNAs derived from each lung cancer cell line was reversed transcribed and labeled with biotin. The membrane carrying the double-stranded complementary DNA (cDNA) targets was prehybridized in 7 mL hybridization buffer (5×SSC, 0.1% N-lauroylsarcosine, 0.1% SDS, 1% blocking reagent mixture manufactured by Roche Molecular Biochemicals, and 50 µg/mL salmon sperm DNA) at 68° C. for 1 hour before hybridization. An 80 µL hybridization solution containing human COT-1 DNA in place of salmon sperm DNA and the cDNA probes were sealed with a microarray in a hybridization bag. After hybridization, the membrane was incubated for 2 hours with a 1-mL mixture containing 700×diluted STREP-GAL (1.38 U/mL, enzyme activity) (GIBCO-BRL), 4% polyethylene glycol 8000 (Sigma), and 0.3% BSA in 1×TBS buffer. The color development reactions were then stopped by 1×PBS containing 20 mM EDTA. The quantification was done using the MuCDA program written in-house and available from Academia Sinica (Taipei, Taiwan). The program isolates differentially expressed genes by measuring the integrated density of each spot, performing regression analysis on the integrated density data, and locating the statistical outliers as differentially expressed genes.

Molecular Cloning and Plasmid Constructs. RNA was reverse transcribed using SuperScript II™ RTase (Gibco-BRL, Rockville, Md.) and random hexameric primers. A cDNA encoding the entire human CRMP-1 (GenBank™ accession no. D78012) coding region was amplified from the cDNA of $CL_{1-0}$ by PCR. The primer sequences were as follows: 5' primer: 5'-CTCCGTCCGTGTCTCTATCC-3' (SEQ ID NO: 3, nucleotides 24-43 of D78012); and 3' primer: 5'-CCTCCATCAGCACCAACTAAA-3' (SEQ ID NO: 4, nucleotides 1955-1975 of D78012). The reaction mixture was denatured at 94° C. for 30 seconds, annealed at 55° C. for 30 seconds, and extended at 72° C. for 3 minutes. These reactions were repeated for 30 cycles. A 1952-bp CRMP-1 cDNA fragment was cloned into a TA vector according to the manufacturer's instructions (pGEM-T-Easy™ cloning kit; Promega, Madison, Wis.). Sequence analysis showed 100% homology to the published sequence (Hamajima et al. (1996) *Gene* 180: 157-63) for CRMP-1 cDNA.

pCIneo-CRMP-1 was created by inserting the CRMP-1 cDNA (nucleotides 24-1975 of D78012) between EcoR I and Not I sites of pCI-neo mammalian expression vector (Promega, Madison, Wis.). Partial length CRMP-1 cDNA (nucleotides 376-1975) was inserted into the Pst I and EcoR I sites of pRSET C prokaryotic expression vector (Invitrogen, Carlsbad, Calif.) to construct pRSET-CRMP-1 for production of fusion protein. The coding region of CRMP-1 cDNA (nucleotides 151-1869) was amplified by PCR from pCIneo-CRMP-1 plasmid. The forward primer 5'-ATTGA CTCGAGATGTCGTACCAGGGCAAGAA-3' (SEQ ID NO:5) included nucleotides 151-170 from CRMP-1 sequence and introduced a Xho I site (underlined). The reverse primer 5'-ATATC GAATTCTCAACCGAGGCTGGTGAT-3' (SEQ ID NO:6) is complementary to nucleotides 1852-1869 and introduced an EcoRI site (underlined). For protein localization study, the amplified CRMP-1 fragment was inserted in frame into the Xho I and EcoR I site of a CMV promoter-driven green fluorescent protein (GFP) expression vector-pEGFP-C3 (Clontech, palo Alto, Calif.) yielding pEGFP-CRMP-1. These constructs were isolated from plasmid clones and sequenced on both strands of the double-stranded DNA using an autosequencer (model ABI 377, PE Applied Biosystems, Forster City, Calif.).

Monoclonal Antibody Production. PRSET-CRMP-1 was transformed into *Escherichia coli* strain BL21(DE3)pLysS. The fusion protein (named His-CRMP(amino acids 76-572)) was obtained as inclusion bodies. The inclusion bodies were solubilized and purified by 12.5% SDS-polyacrylamide gel electrophoresis. BALB/c mice (6 weeks old) received a subcutaneous injection of SDS-PAGE purified fusion protein in 0.1 mL Freund's complete adjuvant (Life Technologies, Grand Island, N.Y.) emulsified in 0.1 mL of sterile phosphate-buffered saline (PBS). Mice then received subcutaneous injections of fusion protein in 0.1 mL Freund's incomplete adjuvant (Life Technologies, Grand Island, N.Y.) emulsified in 0.1 mL of sterile PBS every three weeks. We checked antibody titer by Western blotting, using the preimmune serum as a negative control. Splenocytes from one mouse were fused with mouse myeloma in the presence of polyethylene glycol 1500 (Roche GmbH, Mannheim, Germany). Hybridomas were plated in 96-well plates in DMEM and RPMI-1640 (1:1) medium supplemented with 15% NuSerum (Collaborative Research, Bedford, Mass.), and hypoxanthine-aminopterin-thymidine HAT (Sigma, St. Louis, Mo.). Supernatants were screened by Western blot against the His-CRMP (amino acids 76-572) fusion protein.

Northern Hybridization and Western Blot Analysis. Each lane on 0.8% agarose formaldehyde gels was loaded with 20 µg of total RNA, and after electrophoresis in 1×MOPS running buffer, the gels were blotted onto Hybond-$N^+$ nylon membranes (Amersham, Buckinghamshire, United Kingdom) by the capillary method. After U.V. cross-linking the membranes were prehybridized in 5×SSC, 5×Denhardt's solution, 50 mM NapO$_4$ (pH 6.2), 100 µg/mL salmon sperm DNA, and 50% deionized formamide for 4 hours at 42° C. The membranes were then hybridized with $^{32}$P-labelled DNA probes synthesized using the Rediprime DNA labeling system (Amersham, Buckinghamshire, United Kingdom). Hybridization was performed in 5×SSC, 5×Denhardt's solution, 10% Dextran sulfate, 20 mM NapO$_4$ (pH6.2), 100 µg/mL salmon sperm DNA, and 50% deionized formamide for 18 hours at 42° C. The membranes were washed twice in 2×SSC and 0.5% SDS for 15 minutes at room temperature and twice in 0.1×SSC and 0.1% SDS for 30 minutes at 52° C. The membranes were exposed to X-ray film overnight at −70° C. The amount of RNA in each lane was measured by comparison with the signal intensity of Gβ-like probe (a housekeeping gene used as an internal control for RNA quantity). See Shan et al. (1992) *Mol Cell Biol* 12: 5620-31.

The total cell lysates (5 µg of protein) were separated by 12.5% SDS-PAGE, and transferred to a polyvinylidene diflurode membrane (Immobilon-P membrane, Millipore, Bedford, Mass.) by electrotransfer. After blocking with 5% skim milk in 0.1% polysorbate 20 (commercially also known as Tween®20) in PBS solution, the membrane-bound proteins were probed with the monoclonal antibodies. The membrane was washed and horseradish peroxidase-conjugated antimouse secondary antibody (Amersham, Buckinghamshire, United Kingdom) was applied. The protein bands were detected with an enhanced chemiluminescence assay kit (Amersham, Buckinghamshire, United Kingdom), and X-ray film.

Transfection and Selection. Five µg of pCIneo-CRMP-1 plasmid was transfected into 70% confluent CL$_{1-5}$ cells with 20 U LipofectAMINE reagent (Gibco-BRL, Rockville, Md.) as previously described. The CL$_{1-5}$ cells were also transfected with pCI-neo vector containing no insert as controls (mock transfectants). Gentamicin-G418 (Gibco-BRL, Rockville, Md.) was added to a concentration of 500 µg/mL for selection of stable transfectants. The selection medium was changed every 3 days for 3 weeks. Resistant cell clones were isolated and expanded for further characterization. Integration of the transfected plasmid DNA into the chromosomal DNA was confirmed by Northern hybridization. For transient transfections, 70% confluent cultures of CL$_{1-0}$ and CL$_{1-5}$ cells were transfected with pEGFP-CRMP-1 plasmid by the LipofectAMINE reagent. Forty-eight hours later, the living cells were examined directly and photographed using a Zeiss Axiphot epifluoresence microscope equipped with MRC-1000 laser scanning confocal imaging system (Bio-Rad, Rockville Center, N.Y.). See Hong et al. (2000) *Am J Respir Cell Mol Biol* 23: 355-63.

In Vitro Invasion Assay and Cell Growth Assay. The invasiveness of the transfected clones was examined by using a membrane invasion culture system (MICS) (Chu et al. (1997) *Am J Respir Cell Mol Biol* 17: 353-60). In the MICS system, a polycarbonate membrane containing 10 µm pores (Nucleopore Corp., Pleasanton, Calif.) was coated with a mixture of 5 mg/mL Matrigel. The membrane was placed between the upper- and lower-well plates of a MICS chamber. Cells were resuspended in RPMI-1640 containing 10% NuSerum and seeded into the upper wells of the chamber (2.5×10$^4$ cells/well). After incubating for 48 hours at 37° C., cells that had invaded through the coated membrane were removed from the lower wells with 1 mM EDTA in PBS and dot-blotted onto a polycarbonate membrane with 3 µm pores. Blotted cells were stained with propidium iodine (Sigma, St. Louis, Mo.) and the cell number in each blot was counted using PC software (The Analytical Imaging Station; Imaging Research Inc., Ontario, Canada) under a microscope (50×magnification). Each experiment was performed three times with each sample in triplicate.

Cell growth was measured using the modified 3-(4,5-dimethylthiazol-2-yl)-2,5-diphenyltetrazolium bromide (MTT) assay. See, for example, Denizot et al. (1986) *J Immunol Methods* 89:271-7. Cells were seeded onto 96-well plates at 4000 cells per well in culture media (100 µL). The plates were incubated for up to 4 days. In the MTT assay, 10 µL of the MTT solution (5 mg/mL) was added to each well and the cells were cultured for another 4 hours at 37° C. One hundred µL of 0.04 N HCl in isopropanol was then added to each well, and mixed vigorously to solubilize colored crystals produced within the cells. The absorbance at 570 nm to absorbance at 630 nm as reference wave was measured by a multiwell scanning spectrophotometer (Titertek Multiskan, Flow Laboratories, McClean, Va.). Cell viability was examined by trypan blue dye exclusion test. Each data point represents the average of six determinations from at least three replicates of each experiment.

F-actin Staining. Cells grown on coverslips were washed in PBS three times, fixed in 3.7% paraformaldehyde in PBS for 10 minutes, and permeabilized using 0.1% Triton X-100 in PBS for 10 minutes. Non-specific binding sites were blocked by treatment with 5% non-fat milk in PBS for 15 minutes. After a 5-minute wash with PBS, the cells were incubated with rhodamine-conjugated phalloidin 5 U/mL (Molecular probe, Eugene, Oreg.) for 30 minutes. After PBS washes, the cells were mounted on a slide using a mounting medium containing 2% n-propyl gallate, 60% glycerol in PBS, pH 8.0. The cells were examined and photographed using a Zeiss Axiphot epifluoresence microscope, and images were taken using Kodak T-max 400 film.

Patients and Specimens. Eighty consecutive patients who underwent resection for non-small cell lung cancer at National Taiwan University Hospital between September 1994 and December 1996 were included in the study. This investigation was performed after approval by the Institutional Review Board of National Taiwan University Hospital. Written informed consent was obtained from all patients. All of the tumor tissue samples were treatment naive because none of the patients had received neo-adjuvant chemotherapy or radiation therapy before surgery. Specimens of lung cancer tissue and the non-tumor part of the lung obtained at surgery were immediately snap-frozen in liquid nitrogen and stored at −80° C. until use. Histologic classification was performed according to the World Health Organization criteria (World Health Organization (1982) *Am J Clin Pathol* 77: 123-36). Tumor size, local invasion, and lymph node metastasis were determined at pathologic examination. The final disease stage was determined by a combination of surgical and pathologic findings, according to the current tumor-node-metastasis system for lung cancer staging (Mountain (1997) *Chest* 111: 1710-7). The patients consisted of 51 men and 29 women (mean age 62.9±10.5 years). Thirty-eight (38) of these patients had squamous cell carcinoma and 42 had adenocarcinoma. The surgical-pathology stage of disease was I in 31 patients, II in 19 patients, III in 24 patients, and stage IV in 6 patients. Tumor status was T1 in 15 patients, T2 in 42 patients, T3 in 9 patients, and T4 in 14 patients. Forty-two patients had no lymph node metastasis (N0), and 38 had regional or mediastinal lymph node metastasis (N1 in 19 patients, N2 in 18 patients, and N3 in one patient). Follow-up data were obtained from the patients' medical charts and reported from our tumor registry service. Follow-up, ranging from 6.5 to 70 months, lasted until June 2000. Relapse time was calculated from the date of operation to the date of detection of local recurrence or systemic metastasis. Survival time was calculated from the date of operation to the date of death. The relapse time ranged from 2 to 42 months (median: 11.0 months), and the survival time ranged from 6.5 to 53 months (median: 20.5 months). Patients who died of post-operative complications within 30 days after surgery were excluded from the survival analysis.

Real-Time Quantitative Reverse Transcription Polymerase Chain Reaction. Total mRNA was extracted from resected cancer tissue using an RNA extraction kit (RNeasy™ Mini Kit; Qiagen, Valencia, Calif.). The quality of the RNA samples was determined by electrophoresis through agarose gels and staining with ethidium bromide and the 18S and 28S RNA bands were visualized under U.V. light. The standard curve samples used for real-time quantitative RT-PCR were prepared by serial dilution of a specific RNA sample to cover the range of 250 ng, 50 ng, 10 ng, and 2 ng. The serially diluted samples were aliquotted and stored at −80° C. until use. Based on the cDNA sequence of CRMP-1, the primers used for quantitative RT-PCR of CRMP-1 mRNA were as follows: (1) forward primer, 5'-CCACGATGATCATTGACCATGT-3' (SEQ ID NO: 7, exon 3), and (2) reverse primer, 5'-AGGGAGTAATCACAGCAGGATTTG-3' (SEQ ID NO: 8, exon 4) (Torres (1998) DNA Res 5: 393-5). The sequence of the probe used to detect and quantify the RT-PCR product was FAM (carboxyfluorescein) 5'-AGCCTACTGACCTCTTTCGAGAAGTGGCA-3'TAMRA (N,N,N',N'-tetramethyl-6-carboxy-rhodamine) (SEQ ID NO: 9). This sequence, which is specific to CRMP-1 cDNA, was chosen to span the exon 3-exon 4 junction to avoid quantification of the PCR product from contaminating CRMP-1 genomic DNA. The primers and probe used for quantitative RT-PCR of TBP mRNA (internal control, GenBank™ accession no. X54993)) were as described by Bieche et al. (1999) Clin Chem 45: 1148-56. The identities of PCR products were confirmed by DNA sequencing. Each assay included a standard curve, a no-template control, and triplicate total RNA samples. The reaction conditions were as previously described (Yuan et al. (2000) Am J Respir Crit Care Med 162: 1957-63). The fluorescence emitted by the reporter dye was detected on-line in real-time using the ABI prism 7700 sequence detection system (PE Applied Biosystems, Foster City, Calif.).

Statistical Analysis. Where appropriate, the data are presented as the mean±standard deviation (SD). All statistical analyses were performed with SPSS version 8.0. Comparisons of data between groups were made with Student's t test. The paired Kendall's W test was used to compare the −ΔCT of CRMP-1 mRNA expression between tumor samples and paired normal tissues. Fisher's exact test and Student's t test were used to compare the clinicopathologic characteristics of tumors (and patients) with high and low CRMP-1 mRNA expression. Survival curves were obtained by the Kaplan-Meier method and the difference in relapse time between low and high CRMP-1 expression groups was analyzed with the log-rank test, as was the difference in survival. All statistical tests were two-sided. P values less than 0.05 were considered statistically significant.

Results

Identification of differentially expressed CRMP-1 mRNA by CDNA microarray. A CDNA microarray with calorimetric detection was used to identify differentially expressed genes among lung cancer cell lines ($CL_{1-0}$, $CL_{1-1}$, $CL_{1-5}$, and $CL_{1-5}$-$F_4$) with varying degrees of invasive properties. These four cell lines are invasive to different degrees. Ordered by invasiveness, the four cell lines follow the trend: $CL_{1-0}$< $CL_{1-1}$<$CL_{1-5}$≦$CL_{1-5}$-$F_4$. All experiments of CDNA microarray were performed three times. Cell lines were grown in three independent cultures, and the entire process was carried out independently from RNA extraction to image analysis. The standard deviation of the experiments was 7.3%. Cluster analysis of CDNA microarray data revealed that about 500 genes correlated positively or negatively with the invasiveness of cancer cells. Most of these genes were involved in angiogenesis, cell motility, adhesion, and proliferation. Among them, the mRNA expression of CRMP-1 was correlated negatively with cell line invasiveness.

Northern hybridization confirmed that the level of CRMP-1 expression was drastically reduced in $CL_{1-5}$ and $CL_{1-5}$-$F_4$ relative to $CL_{1-0}$ and $CL_{1-1}$. To confirm that the differential expression of CRMP-1 at the mRNA level was also reflected at the protein level, Western blot analyses was performed using a specific monoclonal antibody-Y21 against CRMP-1. Monoclonal antibody-Y21 recognized CRMP-1 but not other CRMPs. Reduced expression of CRMP-1 in $CL_{1-5}$ and $CL_{1-5}$-$F_4$ was consistently observed.

Over-expression of CRMP-1 can inhibit invasion of carcinoma cells in vitro. To investigate whether a causal relationship exists between the invasion phenotype and CRMP-1 expression, a plasmid construct harboring CRMP-1 cDNA in pCI-neo vector was made and transfected into $CL_{1-5}$, and five clones that stably expressed CRMP-1 were isolated. Northern hybridization was performed to analyze CRMP-1 expression in mock transfectant and CRMP-1 cDNA transfected clones (B5, C6, C8, C10, and C22). The full coding region of CRMP-1 cDNA, 1.95 kb, was used as a probe. All five CRMP-1 transfected clones expressed CRMP-1 mRNA transcripts. In contract, the mock transfectant did not have any detectable CRMP-1 transcripts. A Gβ-like probe was used as an internal control for RNA quality. Western blotting was also performed to analyze CRMP-1 expression in mock transfectant and five CRMP-1 transfected clones. CRMP-1 monoclonal antibody-Y21 was used as the primary antibody. CRMP-1 protein was expressed in CRMP-1 transfected clones, but not in mock transfectant. An in vitro reconstituted basement membrane invasion assay was used to determine whether CRMP-1 expression affected cancer cell invasion. Expression of CRMP-1 suppressed the in vitro invasion ability in $CL_{1-5}$ cells. To facilitate the comparison of the relative invasiveness between mock transfectant and CRMP-1-transfected clones (B5, C6, C8, C10, and C22), all values were normalized to the percent of relative invasion ability compared with the mock transfectant (100%). Each clone was assayed three times in triplicate. After 48 hours incubation, a significant reduction (40% to 60%) in invasive potential was noted in CRMP-1 expressing clones (P<0.01). However, there was a threshold level of CRMP-1 beyond which no further suppression of invasion occurred.

Tumor cells must complete a complex series of steps to invade and metastasize; one of the most basic steps is cell growth. A modified MTT assay was used to measure in vitro cell growth rates of CRMP-1 transfectants and mock transfectant. The fact that In vitro proliferation was not significantly changed by altering CRMP-1 expression, indicated that CRMP-1 may regulate cell invasion by a mechanism other than controlling cell proliferation.

Alteration of F-actin polymerization in CRMP-1 over-expressed cells. F-actin is continuously polymerized and depolymerized in motile cells (Symons & Mitchison (1991) *J Cell Biol* 114: 503-13). Actin polymerization correlates temporally and spatially with lamellar protrusion in motile cells and plays a key role in the process of cell motility (Cooper (1991) *Ann Rev Physol* 53: 585-605), thereby affecting tumor invasion. Phalloidin binds tightly to the actin subunits in filaments but not to the monomers. $CL_{1-0}$, $CL_{1-1}$, $CL_{1-5}$, and $CL_{1-5}$-$F_4$ were stained with rhodamine-conjugated phalloidin and the cells were observed under fluorescence microscopy. The amount of filopodia was much less in $CL_{1-0}$ than $CL_{1-5}$ or $CL_{1-5}$-$F_4$. The F-actin of the transfected cell clones was also stained. CRMP-1 transfected cells were observed that they had higher expression levels in less invasive cell lines and were round. Numerous filopodia were detected in mock transfectant, the same as in parental $CL_{1-5}$. Interestingly, the CRMP-1 transfected $CL_{1-5}$ showed a remarkable decrease in their filopodia projections, similar to that of $CL_{1-0}$.

Dynamic distribution of CRMP-1 within the cells and association of CRMP-1 with mitotic spindle. To determine the intracellular localization of CRMP-1 during different stages of the cell cycle, the full coding region of CRMP-1 cDNA was cloned in a mammalian transfection vector to express an enhanced green fluorescent protein (EGFP) tagged CRMP-1 in $CL_{1-0}$ and $CL_{1-5}$. Fluorescent images obtained by laser scanning confocal microscopy revealed that the distributions of EGFP-tagged CRMP-1 in $CL_{1-0}$ and $CL_{1-5}$ were the same. At interphase, CRMP-1 was diffusely distributed in the cytoplasm. This distribution was distinct from that of microtubules, and F-actin. However, in some EGFP-CRMP-1 transfected cells CRMP-1 was located in the cytoplasm as well as in the nucleus. At prophase, certain CRMP-1 proteins accumulated at the centrosomes. During metaphase, the majority of CRMP-1 was strongly associated with mitotic spindle, and was also concentrated at the centrosomes. During anaphase, CRMP-1 maintained its association with mitotic spindle. During very late telophase, it condensed at the midbody.

CRMP-1 mRNA expression in lung cancer tissue correlates with postoperative relapse and survival in lung cancer patients. Real-time quantitative RT-PCR was used to quantify the transcript copy number of CRMP-1. The threshold cycle (CT) was defined as the fractional cycle number at which the fluorescence generated by cleavage of the probe exceeds a fixed threshold above baseline. For a chosen threshold, a smaller starting copy number results in a higher $C_T$ value. In this study, TATA-box binding protein (TBP) mRNA was used as an internal control (Bieche et al. (1999) *Clin Chem* 45: 1148-56). The relative amount of tissue CRMP-1 mRNA, standardized against the amount of TBP mRNA, was expressed as $-\Delta CT = -[CT_{CRMP-1} - CT_{TBP}]$. The ratio of CRMP-1 mRNA copies/TBP mRNA copies was then calculated as $2^{-\Delta CT} \times K$ (K: constant) (Yuan et al. (2000) *Am J Respir Crit Care Med* 162: 1957-63). The CRMP-1 mRNA expression measured in all 80 tumor samples was significantly lower than in adjacent normal tissue (P<0.001, paired Kendall's W test; two-sided). The $-\Delta CT$ of the 80 tumor samples ranged from $-5.67$ to $3.73$, with a mean of $-1.94 \pm 2.11$ (mean±SD) and a median of $-1.95$. The median value was used to classify patients as a high-expression group or a low-expression group (Table 1). Members of the low-expression group were more likely than those of the high-expression group to have advanced (stage III or IV) disease (P=0.010) and lymph node metastasis (N1, N2 and N3) (P=0.043) (Table 1). The median duration to postoperative recurrence was also longer in the high-expression group (30.5 months; 95% confidence interval [CI]=5.6-55.5 months) than in the low-expression group (15.9 months; 95% CI=8.3-23.5 months) (log-rank test, P=0.030). The high-expression group (the probability of survival leveled off at 0.52) had a significantly longer survival than the low-expression group (median survival was 17.9 months; 95% CI=20.83-35.0 months) (log-rank test, P=0.016). See also FIG. 1 of U.S. application Ser. No. 60/301,075, filed Jun. 26, 2001.

TABLE 1

Clinicopathologic Characteristics of Tumors with High and Low CRMP-1 mRNA Expression.

|  | CRMP-1 mRNA $-\Delta CT < -1.95$ No. of patients | CRMP-1 mRNA $-\Delta CT > -1.95$ No. of patients | P value |
|---|---|---|---|
| Mean age (yrs) | 62 ± 10 | 63 ± 11 | 0.627* |
| Sex |  |  |  |
| Male | 24 | 27 | 0.642 |
| Female | 16 | 13 |  |
| Stage |  |  |  |
| I-II | 19 | 31 | 0.010 |
| III-IV | 21 | 9 |  |
| Tumor status |  |  |  |
| T1-2 | 25 | 32 | 0.137 |
| T3-4 | 15 | 8 |  |
| Nodal status |  |  |  |
| N0 | 16 | 26 | 0.043 |
| N1-3 | 24 | 14 |  |
| Histology |  |  |  |
| Squamous cell CA | 16 | 22 | 0.263 |
| Adenocarcinoma | 24 | 18 |  |

*derived using Student's t test; other P values derived using Fisher's exact test.
CA = carcinoma

OTHER EMBODIMENTS

All of the features disclosed in this specification may be used in any combination. Each feature disclosed in this specification may be replace by an alternative feature serving the same, equivalent, or similar purpose.

From the above description, one skilled in the art can easily ascertain the essential characteristics of the present invention, and without departing from the spirit and scope thereof, can make various changes and modifications of the invention to adapt it to various usages and conditions. Accordingly, other embodiments are also within the scope of the following claims.

What is claimed is:

1. A method for categorizing a lung tumor as having invasive or metastatic potential in a subject comprising:
determining a level of a mRNA encoding a polypeptide comprising the amino acid sequence of SEQ ID NO: 2 in a first sample cell from said subject; wherein said first sample cell is obtained from a biopsied tissue containing lung tumor cells of said subject; and wherein said lung tumor cells are lung adenocarcinoma cells;
determining a level of mRNA expressed by said mRNA in a second sample cell from said subject; wherein said second sample cell is obtained from normal cells of said subject;
comparing said level of mRNA in said first sample cell with said level of mRNA in said second sample cell;
and categorizing said lung tumor as having invasive or metastatic potential in said subject when the level of mRNA in the first sample cell is lower than the level of mRNA in the second sample cell.

2. The method of claim 1 wherein the subject is a human.

3. The method of claim 1, wherein said mRNA comprises a nucleic acid sequence that corresponds to the DNA nucleic acid sequence of SEQ ID NO:1.

4. The method of claim 1, wherein said lung tumor having invasive or metastatic potential is associated with advanced tumor, lymph node metastasis, early post-operative relapse, and short survival.

* * * * *

SEQUENCE LISTING

<160> NUMBER OF SEQ ID NOS: 9

<210> SEQ ID NO 1
<211> LENGTH: 1719

```
<212> TYPE: DNA
<213> ORGANISM: Homo sapiens

<400> SEQUENCE: 1
atgtcgtacc agggcaagaa gagcatcccg cacatcacga gtgaccgact cctcatcaaa      60
ggtggacgga tcatcaacga tgaccaatcc ctttatgctg acgtctacct ggaggatgga     120
cttatcaaac aaataggaga gaacttaatc gttcctggtg gagtgaagac cattgaagcc     180
aacgggcgga tggttattcc cggaggtatt gatgtcaaca cgtacctgca gaagccctcc     240
caggggatga ctgcggctga tgacttcttc aagggacca gggcggcact ggtgggcggg      300
accacgatga tcattgacca tgttgttcct gaacctgggt ccagcctact gacctctttc     360
gagaagtggc acgaagcagc tgacaccaaa tcctgctgtg attactccct ccacgtggac     420
atcacaagct ggtacgatgg cgttcgggag gagctggagg tgctggtgca ggacaaaggc     480
gtcaattcct tccaagtcta catggcctat aaggatgtct accaaatgtc cgacagccag     540
ctctatgaag cctttacctt ccttaagggc ctgggagctg tgatcttggt ccatgcagaa     600
aatggagatt tgatagctca ggaacaaaag cggatcctgg agatgggcat cacgggtccc     660
gagggccatg ccctgagcag acctgaagag ctggaggccg aggcggtgtt ccgggccatc     720
accattgcgg ccggatcaa ctgccctgtg tacatcacca aggtcatgag caagagtgca      780
gccgacatca tcgctctggc caggaagaaa gggcccctag ttttttggaga gcccattgcc     840
gccagcctgg ggaccgatgg cacccattac tggagcaaga actgggccaa ggctgcggcg     900
ttcgtgactt cccctcccct gagcccggac cctaccacgc ccgactactt gacctcccta     960
ctggcctgtg ggacttgca ggtcacaggc agcggccact gtccctacag cactgcccag    1020
aaggcggtgg gcaaggacaa ctttaccctg atccccgagg gtgtcaacgg atagaggag     1080
cggatgaccg tcgtctggga caaggcggtg gctactggca aaatggatga gaaccagttt    1140
gtcgctgtca ccagcaccaa tgcagccaag atctttaacc tgtacccaag gaaagggcgg    1200
attgccgtgg gctcggatgc cgacgtggtc atctgggacc ccgacaagtt gaagaccata    1260
acagccaaaa gtcacaagtc ggcggtggag tacaacatct tcgagggtat ggagtgccac    1320
ggctccccac tagtggtcat cagccagggc aagatcgtct ttgaagacgg aaacatcaac    1380
gtcaacaagg gcatgggccg cttcattccg cggaaggcgt tcccggagca cctgtaccag    1440
cgcgtcaaaa tcaggaataa ggtttttgga ttgcaagggg tttccagggg catgtatgac    1500
ggtcctgtgt acgaggtacc agctacaccc aaatatgcaa ctcccgctcc ttcagccaaa    1560
tcttcgcctt ctaaacacca gcccccaccc atcagaaacc tccaccagtc aacttcagc    1620
ttatcaggtg cccagataga tgacaacaat cccaggcgca ccggccaccg catcgtggcg    1680
cccctggtg gccgctccaa catcaccagc ctcggttga                            1719

<210> SEQ ID NO 2
<211> LENGTH: 572
<212> TYPE: PRT
<213> ORGANISM: Homo sapiens

<400> SEQUENCE: 2

Met Ser Tyr Gln Gly Lys Lys Ser Ile Pro His Ile Thr Ser Asp Arg
 1               5                  10                  15

Leu Leu Ile Lys Gly Gly Arg Ile Ile Asn Asp Asp Gln Ser Leu Tyr
            20                  25                  30

Ala Asp Val Tyr Leu Glu Asp Gly Leu Ile Lys Gln Ile Gly Glu Asn
        35                  40                  45
```

```
Leu Ile Val Pro Gly Val Lys Thr Ile Glu Ala Asn Gly Arg Met
     50                  55                  60

Val Ile Pro Gly Gly Ile Asp Val Asn Thr Tyr Leu Gln Lys Pro Ser
 65                  70                  75                  80

Gln Gly Met Thr Ala Asp Asp Phe Phe Gln Gly Thr Arg Ala Ala
                 85                  90                  95

Leu Val Gly Gly Thr Thr Met Ile Ile Asp His Val Val Pro Glu Pro
                100                 105                 110

Gly Ser Ser Leu Leu Thr Ser Phe Glu Lys Trp His Glu Ala Ala Asp
                115                 120                 125

Thr Lys Ser Cys Cys Asp Tyr Ser Leu His Val Asp Ile Thr Ser Trp
    130                 135                 140

Tyr Asp Gly Val Arg Glu Leu Glu Val Leu Val Gln Asp Lys Gly
145                 150                 155                 160

Val Asn Ser Phe Gln Val Tyr Met Ala Tyr Lys Asp Val Tyr Gln Met
                165                 170                 175

Ser Asp Ser Gln Leu Tyr Glu Ala Phe Thr Phe Leu Lys Gly Leu Gly
                180                 185                 190

Ala Val Ile Leu Val His Ala Glu Asn Gly Asp Leu Ile Ala Gln Glu
    195                 200                 205

Gln Lys Arg Ile Leu Glu Met Gly Ile Thr Gly Pro Glu Gly His Ala
    210                 215                 220

Leu Ser Arg Pro Glu Glu Leu Glu Ala Glu Ala Val Phe Arg Ala Ile
225                 230                 235                 240

Thr Ile Ala Gly Arg Ile Asn Cys Pro Val Tyr Ile Thr Lys Val Met
                245                 250                 255

Ser Lys Ser Ala Ala Asp Ile Ile Ala Leu Ala Arg Lys Lys Gly Pro
                260                 265                 270

Leu Val Phe Gly Glu Pro Ile Ala Ala Ser Leu Gly Thr Asp Gly Thr
                275                 280                 285

His Tyr Trp Ser Lys Asn Trp Ala Lys Ala Ala Phe Val Thr Ser
    290                 295                 300

Pro Pro Leu Ser Pro Asp Pro Thr Thr Pro Asp Tyr Leu Thr Ser Leu
305                 310                 315                 320

Leu Ala Cys Gly Asp Leu Gln Val Thr Gly Ser Gly His Cys Pro Tyr
                325                 330                 335

Ser Thr Ala Gln Lys Ala Val Gly Lys Asp Asn Phe Thr Leu Ile Pro
                340                 345                 350

Glu Gly Val Asn Gly Ile Glu Glu Arg Met Thr Val Val Trp Asp Lys
                355                 360                 365

Ala Val Ala Thr Gly Lys Met Asp Glu Asn Gln Phe Val Ala Val Thr
    370                 375                 380

Ser Thr Asn Ala Ala Lys Ile Phe Asn Leu Tyr Pro Arg Lys Gly Arg
385                 390                 395                 400

Ile Ala Val Gly Ser Asp Ala Asp Val Val Ile Trp Asp Pro Asp Lys
                405                 410                 415

Leu Lys Thr Ile Thr Ala Lys Ser His Lys Ser Ala Val Glu Tyr Asn
                420                 425                 430

Ile Phe Glu Gly Met Glu Cys His Gly Ser Pro Leu Val Val Ile Ser
                435                 440                 445

Gln Gly Lys Ile Val Phe Glu Asp Gly Asn Ile Asn Val Asn Lys Gly
    450                 455                 460
```

```
Met Gly Arg Phe Ile Pro Arg Lys Ala Phe Pro Glu His Leu Tyr Gln
465                 470                 475                 480

Arg Val Lys Ile Arg Asn Lys Val Phe Gly Leu Gln Gly Val Ser Arg
            485                 490                 495

Gly Met Tyr Asp Gly Pro Val Tyr Glu Val Pro Ala Thr Pro Lys Tyr
        500                 505                 510

Ala Thr Pro Ala Pro Ser Ala Lys Ser Ser Pro Ser Lys His Gln Pro
    515                 520                 525

Pro Pro Ile Arg Asn Leu His Gln Ser Asn Phe Ser Leu Ser Gly Ala
        530                 535                 540

Gln Ile Asp Asp Asn Asn Pro Arg Arg Thr Gly His Arg Ile Val Ala
545                 550                 555                 560

Pro Pro Gly Gly Arg Ser Asn Ile Thr Ser Leu Gly
            565                 570
```

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
ctccgtccgt gtctctatcc                                        20

<210> SEQ ID NO 4
<211> LENGTH: 21
<212> TYPE: DNA
<213> ORGANISM: Artificial Sequence
<220> FEATURE:
<223> OTHER INFORMATION: Primer

<400> SEQUENCE: 4
cctccatcag caccaactaa a                                      21

<210> SEQ ID NO 5
<211> LENGTH: 31
<212> TYPE: DNA
<213> ORGANISM: Artificial Sequence
<220> FEATURE:
<223> OTHER INFORMATION: Primer

<400> SEQUENCE: 5
attgactcga gatgtcgtac cagggcaaga a                           31

<210> SEQ ID NO 6
<211> LENGTH: 29
<212> TYPE: DNA
<213> ORGANISM: Artificial Sequence
<220> FEATURE:
<223> OTHER INFORMATION: Primer

<400> SEQUENCE: 6
atatcgaatt ctcaaccgag gctggtgat                              29

<210> SEQ ID NO 7
<211> LENGTH: 22
<212> TYPE: DNA
<213> ORGANISM: Artificial Sequence
<220> FEATURE:
<223> OTHER INFORMATION: Primer

<400> SEQUENCE: 7

```
ccacgatgat cattgaccat gt                                        22

<210> SEQ ID NO 8
<211> LENGTH: 24
<212> TYPE: DNA
<213> ORGANISM: Artificial Sequence
<220> FEATURE:
<223> OTHER INFORMATION: Primer

<400> SEQUENCE: 8
agggagtaat cacagcagga tttg                                      24

<210> SEQ ID NO 9
<211> LENGTH: 29
<212> TYPE: DNA
<213> ORGANISM: Artificial Sequence
<220> FEATURE:
<223> OTHER INFORMATION: Probe

<400> SEQUENCE: 9
agcctactga cctctttcga gaagtggca                                 29
```